US008865440B2

(12) United States Patent
Brown et al.

(10) Patent No.: US 8,865,440 B2
(45) Date of Patent: Oct. 21, 2014

(54) MICROORGANISMS HAVING ENHANCED RESISTANCE TO ACETATE AND METHODS OF USE

(71) Applicant: UT-Battelle, LLC, Oak Ridge, TN (US)

(72) Inventors: Steven D. Brown, Knoxville, TN (US); Shihui Yang, Knoxville, TN (US)

(73) Assignee: UT-Batelle, LLC, Oakridge, TN (US)

( * ) Notice: Subject to any disclaimer, the term of this patent is extended or adjusted under 35 U.S.C. 154(b) by 0 days.

(21) Appl. No.: 13/688,636

(22) Filed: Nov. 29, 2012

(65) Prior Publication Data

US 2013/0078691 A1    Mar. 28, 2013

Related U.S. Application Data

(62) Division of application No. 12/770,025, filed on Apr. 29, 2010, now abandoned.

(60) Provisional application No. 61/173,649, filed on Apr. 29, 2009.

(51) Int. Cl.
| | |
|---|---|
| *C12P 7/06* | (2006.01) |
| *C12P 7/08* | (2006.01) |
| *C12P 7/10* | (2006.01) |
| *C12N 1/22* | (2006.01) |
| *C12N 1/21* | (2006.01) |
| *C12N 1/19* | (2006.01) |
| *C12P 7/02* | (2006.01) |
| *C12P 7/04* | (2006.01) |
| *C07K 14/395* | (2006.01) |
| *C12P 7/16* | (2006.01) |
| *C07K 14/39* | (2006.01) |

(52) U.S. Cl.
CPC .. *C12P 7/02* (2013.01); *Y02E 50/17* (2013.01); *C12P 7/10* (2013.01); *C12P 7/04* (2013.01); *C07K 14/395* (2013.01); *Y02E 50/10* (2013.01); *Y02E 50/16* (2013.01); *C12P 7/16* (2013.01); *C07K 14/39* (2013.01); *C12P 7/065* (2013.01)
USPC ........... 435/165; 435/161; 435/163; 435/252; 435/252.3; 435/254.11

(58) Field of Classification Search
None
See application file for complete search history.

(56) References Cited

U.S. PATENT DOCUMENTS

| | | |
|---|---|---|
| 5,514,583 A | 5/1996 | Picataggio et al. |
| 5,712,133 A | 1/1998 | Picataggio et al. |
| 5,726,053 A | 3/1998 | Picataggio et al. |
| 5,843,760 A | 12/1998 | Xhang et al. |
| 7,285,403 B2 | 10/2007 | Jeffries et al. |

FOREIGN PATENT DOCUMENTS

WO    WO 2009012210 A2 *    1/2009

OTHER PUBLICATIONS

Mirisola et al. Yeast vectors for the integration/expression of any sequence at the TYR1 locus. Yeast, vol. 24, pp. 761-766, Jun. 2007.*

Wu, L. et al., "Over-Expression of the Bacterial nhaA Gene in Rice Enhances Salt and Drought Tolerance" Plant Science (2005) pp. 297-302, vol. 168(2).
Yang, S. et al., "Transcriptomic and Metabolomic Profiling of *Zymomonas mobilis* During Aerobic and Anaerobic Fermentations" BMC Genomics (2009) pp. 1-16, vol. 10(34).
Zhang, M. et al., "Metabolic Engineering of a Pentose Metabolism Pathway in Ethanologenic *Zymomonas mobilis*" Science (1995) pp. 240-243, vol. 267.
Product Information for Open Biosystems Product No. YSC4515, printed from https://www.openbiosystems.com/collateral/genomics/pi/Yeast_manuals/Yeast_GST_%20Manual.psf as pp. 1/5 to 5/5 on Jul. 24, 2012.
Sopko et al. Mapping pathways and phenotypes by systematic gene overexpression. Molecular Cell, vol. 21, pp. 319-330, Feb. 2006.
Cartharius et al. MatInspector and beyond: promoter analysis based on transcription factor binding sites, Bioinformatics, vol. 21, No. 13, pp. 2933-2942, 2005.
Alexeyev, M.F., "The pKNOCK Series of Broad-host-range Mobilizable Suicide Vectors for Gene Knockout and Targeted DNA Insertion into the Chromosome of Gram-negative Bacteria" Biotechniques (1999) pp. 824-826, vol. 26.
Almeida, J.R.M. et al., "Increased Tolerance and Conversion of Inhibitors in Lignocellulosic Hydrolysates by *Saccharomyces cerevisiae*" Journal of Chemical Technology and Biotechnology (2007) pp. 340-349, vol. 82(4).
Arkin, .IT. et al., "Mechanism of Na+/H+ Antiporting" Science (2007) pp. 799-803, vol. 317.
Banuelos, M.A. et al., "The Nha1 Antiporter of *Saccharomyces cerevisiae* Mediates Sodium and Potassium Efflux" Microbiology (1998) pp. 2749-2758, vol. 144.
Cagnac, O. et al., "Identification and Characterization of Vnx1p, a Novel Type of Vacuolar Monovalent Cation/H+ Antiporter of *Saccharomyces cerevisiae*" Journal of Biological Chemistry (2007) pp. 24284-24293, vol. 282.
Baumler, D.J. et al., "Enhancement of Acid Tolerance in *Zymomonas mobilis* by a Proton-buffering Peptide" Applied Biochemistry and Biotechnology (2006) pp. 15-26, vol. 134(1).
Chinnawirotpisan, P. et al., "Quinoprotein Alcohol Dehydrogenase is Involved in Catabolic Acetate Production, While NAD-dependent Alcohol Dehydrogenase in Ethanol Assimilation in Acetobacter Pasteurianus SKU1108" Journal of Bioscience and Bioengineering (2003) pp. 564-571, vol. 96(6).
Deanda, K. et al., "Development of an Arabinose-Fermenting *Zymomonas mobilis* Strain by Metabolic Pathway Engineering" Applied and Environmental Microbiology (1996) pp. 4465-4470, vol. 62(12).

(Continued)

*Primary Examiner* — Jennifer Dunston
(74) *Attorney, Agent, or Firm* — Scully, Scott, Murphy & Presser, P.C.

(57) ABSTRACT

The present invention provides isolated or genetically modified strains of microorganisms that display enhanced resistance to acetate as a result of increased expression of a sodium proton antiporter. The present invention also provides methods for producing such microbial strains, as well as related promoter sequences and expression vectors. Further, the present invention provides methods of producing alcohol from biomass materials by using microorganisms with enhanced resistance to acetate.

12 Claims, 18 Drawing Sheets

(56) References Cited

OTHER PUBLICATIONS

Denef, V.J. et al. "Genetic and Genomic Insights into the Role of Benzoate Catabolic Pathway Redundancy in *Burkholderia xenovorans* LB400" Applied and Environmental Microbiology (2006) pp. 585-595, vol. 72(1).

Dien, B.S. et al., "Bacteria Engineered for Fuel Ethanol Production: Current Status" Applied Microbiological Biotechnology (2003) pp. 258-266, vol. 63(3).

Fukaya, M. et al., "Cloning of Genes Responsible for Acetic Acid Resistance in *Acetobacter aceti*" Journal of Bacteriology (1990) pp. 2096-2104, vol. 172(4).

Fukaya, M. et al., "The aarC Gene Responsible for Acetic Acid Assimilation Confers Acetic Acid Resistance on *Acetobacter aceti*" Journal of Fermentation and Bioengineering (1993) pp. 270-275, vol. 76(4).

Gao, X. et al., "Overexpression of SOD2 Increases Salt Tolerance of *Arabidopsis*" Plant Physiology (2003) pp. 1873-1881, vol. 133(4).

Gunasekaran, P. et al., "Ethanol Fermentation Technology-Zymomonas Mobilis" Current Science (1999) pp. 56-68, vol. 77(1).

Hahnenberger, K.M. et al., "Functional Expression of the Schizosaccharomyces Pombe Na+/H+ Antiporter Gene, sod2, in *Saccharomyces cerevisiae*" Proceedings of the National Academy of Sciences of the United States of America (1996) pp. 5031-5036, vol. 93(10).

Jeon, Y.J. et al., "Kinetic Analysis of Ethanol Production by an Acetate-Resistant Strain of Recombinant *Zymomonas mobilis*" Biotechnology Letters (2002) pp. 819-824, vol. 24(10).

Jia, Z.P. et al., "Gene Amplification at a Locus Encoding a Putative Na+/H+ Antiporter Confers Sodium and Lithium Tolerance in Fission Yeast" The EMBO Journal (1992) pp. 1631-1640, vol. 11(4).

Joachimstahl, E. et al., "A Mutant of *Zymomonas mobilis* ZM4 Capable of Ethanol Production from Glucose in the Presence of High Acetate Concentrations" Biotechnology Letters (1998) pp. 137-142, vol. 20(2).

Joachimsthal, E. et al., "Characterization of a High-Productivity Recombinant Strain of *Zymomonas mobilis* for Ethanol Production From Glucose/Xylose Mixtures" Applied Biochemistry and Biotechnology (2000) pp. 343-356, vol. 84(6).

Kadar, Z. et al. "Ethanol Fermentation of Various Pretreated and Hydrolyzed Substrates at Low Initial pH" Applied Biochemistry and Biotechnology (2007) pp. 847-858, vol. 137.

Kim, I.S. et al., "Nuclear Magnetic Resonance Studies of Acetic Acid Inhibition of Rec *Zymomonas mobilis* ZM4(pZB5)" Applied Biochemistry and Biotechnology (2000) pp. 357-370, vol. 84-6.

Lawford, H.G. et al., "The Effect of Acetic Acid on Fuel Ethanol-Production by *Zymomonas*" Applied Biochemistry and Biotechnology (1993) pp. 687-699, vol. 39.

Lawford, H.G. et al., "Effects of pH and Acetic Acid on Glucose and Xylose Metabolism by a Genetically Engineered Ethanologenic *Escherichia coli*." Applied Biochemistry and Biotechnology (1993) pp. 301-322, vol. 39/40.

Lawford, H.G. et al., "Improving Fermentation Performance of Recombinant *Zymomonas* in Acetic Acid-Containing Media" Applied Biochemistry and Biotechnology (1998) pp. 161-172, vol. 70-72.

Lawford, H.G. et al., "Fermentation Performance Assessment of a Genomically Integrated Xylose-Utilizing Recombinant of *Zymomonas mobilis* 39676" Applied Biochemistry and Biotechnology (2001) pp. 117-131, vol. 91-93.

Lawford, H.G. et al., "Cellulosic Fuel Ethanol—Alternative Fermentation Process Designs with Wild-Type and Recombinant *Zymomonas mobilis*" Applied Biochemistry and Biotechnology (2003) pp. 457-469, vol. 105-108.

Lawford, H.G. et al., "Fermentation Performance Characteristics of a Prehydrolyzate-Adapted Xylose-Fermenting Recombinant *Zymomonas* in Batch and Continuous Fermentations" Applied Biochemistry and Biotechnology (1999) pp. 191-204, vol. 77-79.

Lawford, H.G. et al., "Comparative Ethanol Productivities of Different *Zymomonas* Recombinants Fermenting Oat Hull Hydrolysate" Applied Biochemistry and Biotechnology (2001) pp. 133-146, vol. 91-93.

Lawford, H.G. et al., "Performance Testing of *Zymomonas mobilis* Metabolically Engineered for Confermentation of Glucose, Xylose, and Arabinose" Applied Biochemistry and Biotechnology (2002) pp. 429-448, vol. 98-100.

Liu, Z.L. et al., "Enhanced Biotransformation of Furfural and Hydroxymethylfurfural by Newly Developed Ethanologenic Yeast Strains" Applied Biochemistry and Biotechnology (2005) pp. 451-460, vol. 121.

Matsushita, K. et al., "*Acetobacter aceti* Possesses a Proton Motive Force-Dependent Efflux System for Acetic Acid" Journal of Bacteriology (2005) pp. 4346-4352, vol. 187(13).

McMillan, J.D. "Conversion of Hemicellulose Hydrolyzates to Ethanol" Enzymatic Conversion of Biomass for Fuels Production (1994) pp. 411-437, Chapter 21.

Mohagheghi, A. et al., "Performance of a Newly Developed Integrant of *Zymomonas mobilis* for Ethanol Production on Corn Stover Hydrolysate" Biotechnology Letters (2004) pp. 321-325, vol. 26(4).

Mohagheghi, A. et al., "Cofermentation of Glucose, Xylose, and Arabinose by Genomic DNA-Integrated Xylose/Arabinose Fermenting Strain of *Zymomonas mobilis* AX101" Applied Biochemistry and Biotechnology (2002) pp. 885-898, vol. 98-100.

Mullins, E.A. et al., "A Specialized Citric Acid Cycle Requiring Succinyl-Coenzyme A (CoA): Acetate CoA-Transferase (AarC) Confers Acetic Acid Resistance on the Acidophile *Acetobacter aceti*" Journal of Bacteriology (2008) pp. 4933-4940, vol. 190(14).

Okumura, H. et al., "Biochemical Characteristics of Spontaneous Mutants of *Acetobacter aceti* Deficient in Ethanol Oxidation" Agricultural Biological Chemistry (1985) pp. 2485-2487, vol. 49(8).

Panesar, P. S. et al., "*Zymomonas mobilis:* an Alternative Ethanol Producer" Journal of Chemical Technology and Biotechnology (2006) pp. 623-635, vol. 81(4).

Pelletier, D.A. et al., "A General System for Studying Protein-Protein Interactions in Gram-Negative Bacteria" Journal of Proteome Research (2008) pp. 3319-3328, vol. 7(8).

Prior, C. et al., "Characterization of the NHA1 Gene Encoding a Na+/H+-Antiporter of the Yeast *Saccharomyces cerevisiae*" FEBS Letters (1996) pp. 89-93, vol. 387.

Ranatunga, T.D. et al., "Identification of Inhibitory Components Toxic Toward *Zymomonas mobilis* CP4(pZB5) Xylose Fermentation" Applied Biochemistry and Biotechnology (1997) pp. 185-198, vol. 67(3).

Reisch, M. "Fuels of the Future Chemistry and Agriculture Join to Make a New Generation of Renewable Fuels" Chemical and Engineering News (2006) pp. 30-32, vol. 84(7).

Rogers, P.L. et al., "*Zymomonas* Ethanol Fermentations" Microbiological Sciences (1984) pp. 133-136, vol. 1(6).

Rogers, P.L. et al., "*Zymomonas mobilis* for Fuel Ethanol and Higher Value Products" Advanced Biochemistry Engineering and Biotechnology (2007) pp. 263-288, vol. 108.

Steiner, P. et al., "Overexpression of the ATP-Dependent Helicase RecG Improves Resistance to Weak Organic Acids in *Escherichia coli*" Applied Microbiology and Biotechnology (2003) pp. 293-299, vol. 63(3).

Swings, J. et al., "The Biology of *Zymomonas mobilis*" Bacteriological Reviews (1977) pp. 1-46, vol. 41(1).

Takahashi, C.M. et al., "Effects of Acetate on the Growth and Fermentation Performance of *Escherichia coli* KO11" Applied Biochemistry and Biotechnology (1999) pp. 193-203, vol. 81(3).

Takemura, H. et al., "Novel Insertion Sequence IS1380 from Acetobacter Pasteurianus is Involved in Loss of Ethanol Oxidizing Ability" (1991) Journal of Bacteriology (1991) pp. 7070-7076, vol. 173(22).

Nevoigt, E., "Progress in Metabolic Engineering of *Saccharomyces cerevisiae*", Microbiology and Molecular Biology Reviews, 72(3):379-412 (2008).

* cited by examiner atgcggttttctattcgtcgattttttcagctgcctctggcggcgcgattatcctgctcttatccgcccttcttggattgcttttatccaactcttttg
tccgaaagttatttaaggtgcttcatctgaaaatgccatttcggctttggatgatgcccctaatctggcagagtttatttctattgcgccgatgtc
gcttttctttttgtcgttattgcagaaataaaagaagaaattatttcgggacatctggcttctttccggcgggttatcttgcccctgatttcagcttta
gggggaatgatgattcccgcttgtctatatgggctgattacatctggtcatttagaagtaagccgtggctgggcgataccaatcgcaacggat
gccgcctttaccttacctattattttggcgttaggacgccatgttctgaaggcgcaagggtctggttaatggctttggctattttcgatgacctatt
aggtattgttgttattgctcttttttatgcgtcccatttgaatggatatgccctttcgcagcgggcttaatcactgccgtgatgattgggctgaataa
aaaatctgtccagaatttatgggtctatgcttctgctggtgttgtcttatggtgggctctattggtttctggcctccatcctaccatcgccggtgtga
taacaggtcttgcccttccttctgttgcggatcaaccggaaaaagcctctccttagagcgaggaaaacaaattattgcgccttgggtgacatg
gctcattctgcctttatttggctttgttagtatgggaatgtcgctgtctgctatgtcctttcatgttttgctggcacctgtccctttgggggttgcgttg
ggcttgttttggggaaagcccatagggttttggtgctactataatggcaacccgactaaagattgcgaccttcctaagggaacttccttgag
gatgttgttcgggctatccttgttatgcggtatcggttttacgattagtttatttattgcagaattggcttttctggttcagatttctggttccggcca
aatatgggatattgatgggctctctcttatccgctttagctggatggttatggttacgttttttaaagtttccggcaaaaggcgtttga

Figure 4A. Nucleotide sequence of ZM4 *nhaA* gene.

mrfsirrffsaasggaiillsallglllsnsflsesyfkvlhlkmpfsalddapnlaefisiapmslfffvviaeikeeiisghlasfrrvilplisa
lggmmipaclyglitsghlevsrgwaipiatdaaftlpiilalgrhvsegarvwlmalaifddllgivvialfyashlngyalfaaglitavm
iglnkksvqnlwvyasagvvlwwallvsglhptiagvitglalpsvadqpekasplergkqiiapwvtwlilplfgfvsmgmslsams
fhvllapvplgvalglflgkpigvfgatimatrlkiatlpkgtslrmlfglsllcgigftislfiaclafsgsdflvpakygilmgsllsalagwl
wlrflkfpakgv*

Figure 4B. Protein sequence of ZM4 NhaA anti-porter.

MICROORGANISMS HAVING ENHANCED RESISTANCE TO ACETATE AND METHODS OF USE

CROSS REFERENCE TO RELATED APPLICATIONS

This application is a divisional application of U.S. application Ser. No. 12/770,025 filed Apr. 29, 2010, now abandoned, which claims the benefit of priority from U.S. Provisional Application No. 61/173,649, filed on Apr. 29, 2009.

This invention was made with government support under Contract Number DE-ACO5-000R22725 between the United States Department of Energy and UT-Battelle, LLC. The U.S. Government has certain rights in this invention.

FIELD OF THE INVENTION

This invention generally relates to the field of microorganism and genetic modification thereof. In particular, the invention relates to microorganisms that display enhanced resistance to acetate as a result of increased expression of an antiporter gene, and are therefore advantageous for use in fermentation of biomass materials to produce biofuels such as ethanol. Related compositions, including promoter sequences, expression vectors, genetically engineered microbial strains, as well as methods of making and using the strains, are also provided by the invention.

BACKGROUND OF THE INVENTION

Biomass-based bioenergy is crucial to meet the goal of making cellulosic biofuels cost-competitive with gasoline. Lignocellulosic materials represent an abundant feedstock for cellulosic-biofuel production. A core challenge in coverting cellulosic material to biofuels such as ethanol and butanol is the recalcitrance of biomass to breakdown. Because of the complex structure of lignocellulosic biomass, pretreatment is necessary to make it accessible for enzymatic attack. Severe biomass pretreatments are required to release the sugars, which along with by-products of fermentation can create inhibitors in the production of ethanol or butanol, for example. During the pretreatment processes, a range of inhibitory chemicals are formed that include sugar degradation products such as furfural and hydroxymethyl furfural (HMF); weak acids such as acetic, formic, and levulinic acids; lignin degradation products such as the substituted phenolics vanillin and lignin monomers. In addition, the metabolic byproducts such as ethanol, lactate, and acetate also impact the fermentation by slowing and potentially stopping the fermentation prematurely. The increased lag phase and slower growth increases the ethanol cost due to both ethanol production rate and total ethanol yield decreases (Takahashi et al. 1999; Kadar et al. 2007).

Efficient conversion of lignocellulosic hydrolysates to biofuel requires high-yield production and resistance to industrially relevant stresses and inhibitors. To overcome the issue of inhibition caused by pretreatment processes, there are two approaches, one is to remove the inhibitor after pretreatment from the biomass physically or chemically, which requires extra equipment and time leading to increased costs. A second approach utilizes inhibitor tolerant microorganisms for efficient fermentation of lignocellulosic material to ethanol and their utility is considered an industrial requirement (Almeida et al. 2007).

*Z. mobilis* are gram-negative facultative anaerobic bacteria with a number of desirable industrial characteristics, such as high-specific productivity and ethanol yield, unique anaerobic use of the Entner-Doudoroff pathway that results in low cell mass formation, high ethanol tolerance (12%), pH 3.5-7.5 range for ethanol production and has a generally regarded as safe (GRAS) status (Swings and De Ley 1977; Rogers et al. 1984; Gunasekaran and Raj 1999; Dien et al. 2003; Panesar et al. 2006; Rogers et al. 2007). One drawback to using wild-type *Z. mobilis* is its narrow substrate utilization range. However, recombinant *Z. mobilis* strains have been developed to ferment pentose sugars such as xylose and arabinose (Zhang et al. 1995; Deanda et al. 1996; Mohagheghi et al. 2002). A newly formed partnership between the DuPont and Broin companies utilizes recombinant *Z. mobilis* strains for bioethanol fermentation from the lignocellulosic residues such as corn stover (Reisch 2006). On the other hand, low tolerance to acetic acid and decreased ethanol tolerance have been reported in recombinant strains (Ranatunga et al. 1997; Lawford and Rousseau 1998; Lawford et al. 2001; Dien et al. 2003).

Acetic acid is an inhibitor produced by the de-acetylation of hemicelluloses during biomass pretreatment. At pH 5.0, 36% of acetic acid is in the uncharged and undissociated form (HAc) and is able to permeate the *Z. mobilis* plasma membrane (Lawford and Rousseau 1993). The inhibition mechanism has been ascribed to the ability of the undissociated (protonated) form to cross the cell membrane leading to uncoupling and anion accumulation causing cytoplasmic acidification. Its importance comes from the significant concentrations of acetate that are produced relative to fermentable sugars (McMillan 1994) and the ratio of acetate to fermentable sugars is particularly high in material from hardwoods (Lawford and Rousseau 1993). Acetate may reach inhibitory levels when pretreated biomass hydrolysates are concentrated to generate high final ethanol concentrations or where process water is recycled. Acetate removal processes have been described but they are energy or chemical-intensive and their impact on processing costs have yet to be determined (McMillan 1994).

An acetate tolerant *Z. mobilis* mutant (AcR) has been generated by a random mutagenesis and selection strategy (Joachimstahl and Rogers 1998). The AcR mutant was capable of efficient ethanol production in the presence of 20 g/L sodium acetate while the parent ZM4 was inhibited significantly above 12 g/L sodium acetate under the same conditions. A number of studies have characterized the performance of recombinant *Z. mobilis* strains able to utilize both C-5 and C-6 sugars, including under acetate stress conditions (Lawford et al. 1999; Joachimsthal and Rogers 2000; Lawford and Rousseau 2001). Acetic acid was shown to be strongly inhibitory to wild-type derived strain ZM4 (pZB5) on xylose medium and nuclear magnetic resonance studies indicated intracellular deenergization and acidification appeared to be the major inhibition mechanisms (Kim et al. 2000). A recombinant strain able to utilize both xylose (a C-5 sugar) and glucose (a C-6 sugar) with increased acetate resistance was generated by transforming plasmid pZB5 into the AcR background (Jeon et al. 2002). Mohagheghi et al. (2004) reported a recombinant *Zymomonas mobilis* 8b tolerated up to 16 g/L acetic acid and achieved 82%-87% (w/w) ethanol yields from pure glucose/xylose solutions.

Acetic acid bacteria are used for the industrial production of vinegar and are intrinsically resistant to acetic acid. Although the resistance mechanism is not completely understood, progress toward this goal has been made in recent years. Spontaneous acetic acid bacteria mutants for *Acetobacter aceti* (Okumura et al. 1985) and several *Acetobacter pasteurianus* strains (Takemura et al. 1991; Chinnawirotpisan et al. 2003) showed growth defects in the presence of acetic acid, which was associated with loss of alcohol dehydrogenase activity. Fukaya et al (1990) identified the aarA, aarB, and aarC gene cluster as being important for conferring acetic acid resistance using a genetic approach (Fukaya et al. 1990). aarA encodes citrate synthase and aarC encodes a protein that is involved in acetate assimilation (Fukaya et al. 1993) and the three aar genes have been suggested to support increased flux through a complete but unusual citric acid cycle to lower cytoplasmic acetate levels (Mullins et al. 2008). The presence of a proton motive force-dependent efflux system for acetic acid has been demonstrated as being important in *A. aceti* acetic acid resistance, although the genetic determinant(s) remain to be identified (Matsushita et al. 2005). In *E. coli*, over-expression of the ATP-dependent helicase RecG has been reported to improve resistance to weak organic acids including acetate (Steiner and Sauer 2003). Baumler et al. (2006) describe the enhancement of acid tolerance in *Z. mobilis* by the expression of a proton-buffering peptide in acidified TSB (HCl (pH 3.0) or acetic acid (pH 3.5)), glycine-HCl buffer (pH 3.0) and sodium acetate-acetic acid buffer (pH 3.5) (Baumler et al. 2006). Baumler et al. (2006) also note that the presence of the antibiotic also significantly increased acid tolerance by an unknown mechanism.

SUMMARY OF THE INVENTION

It has been identified in accordance with the present invention that increased expression of a sodium-proton antiporter gene in a microorganism confers enhanced acetate resistance to the microorganism. In accordance with the present invention, microorganisms can be genetically modified to increase the expression of its sodium-proton antiporter to achieve enhanced resistance to an acetate salt (e.g., sodium, potassium or ammonium acetate) or acetic acid. Such genetically modified microorganisms are particularly useful for production of biofuels based on fermentation of biomass materials.

In one aspect, the invention is directed to isolated microorganisms that display enhanced resistance to acetate as a result of increased expression of a sodium-proton antiporter in the microorganisms.

In a preferred embodiment, the sodium-proton antiporter being expressed at an elevated level is a plasma membrane sodium-proton antiporter. In other embodiments, the sodium-proton antiporter being expressed at an elevated level is an endosomal or vacuolar sodium-proton antiporter. The sodium-proton antiporter being expressed at an elevated level is preferably encoded by an nhaA gene or an nhaA homolog.

Microorganisms contemplated by the present invention include both bacteria (including Gram-negative and Gram positive bacterial) and fungi. Examples of bacteria of particular interest include *Acetobacterium, Bacillus, Streptococcus, Clostridium, Zymomonas* sp. (e.g., *Z. mobilis*), and *Gluconobacter* sp. Examples of fungi include *Saccharomyces* sp., *Kluyveromyces* sp., *Pichia* sp., *Candida* sp., and *Schizosaccharomycetes* sp.

In a specific embodiment, the microbial strain is a *Z. mobilis* strain that displays enhanced resistance to sodium acetate as a result of increased expression of a sodium-proton antiporter. In another specific embodiment, the microbial strain is a yeast strain such as a *Saccharomyces* or *Pichia* strain, which displays enhanced resistance to one or more acetate salts as a result of increased expression of a sodium-proton antiporter.

In one embodiment, a microbial strain having enhanced resistance to acetate is created by genetically modifying the 5' upstream region of the endogenous nhaA gene of the strain.

In a specific embodiment, the microbial strain is a *Z. mobilis* strain, wherein the 5' upstream region of the nhaA gene is modified such that a nucleotide sequence of 1000 bp or less containing SEQ ID NO: 4 is deleted, while the nucleotide sequence of SEQ ID NO: 4 immediately 5' to the nhaA coding sequence remains intact. Such *Z. mobilis* strain displays constitutive and elevated expression of nhaA, and enhanced resistance to sodium acetate.

Isolated nucleic acids containing a nucleotide sequence of SEQ ID NO: 4 or SEQ ID NO: 5, or derivatives thereof, form separate embodiments of the present invention.

In another embodiment, a microbial strain having enhanced resistance to acetate is created by introducing an exogenous expression vector into the strain which directs expression (i.e., additional expression) of a sodium-proton antiporter. Preferably, the sodium proton antiporter expressed from the exogenous vector is identical with an endogenous sodium proton antiporter, particularly an endogenous plasma membrane sodium proton antiporter.

The genetically modified microorganisms that display enhanced resistance to acetate as a result of increased expression of a sodium-proton antiporter can be additionally modified as appropriate, for example, by transformation with additional recombinant genes or sequences suitable for fermentation and production of ethanol.

In a further aspect, the present invent provides a method of producing biofuels from cellulosic biomass based on use of the microbial strains that are able to grow at elevated concentrations of acetate or acetic acid.

BRIEF DESCRIPTION OF THE DRAWINGS

FIGS. 4A-4B set forth the nucleotide sequence (SEQ ID NO: 1) and protein sequence (SEQ ID NO: 2) of ZMO0119.

DETAILED DESCRIPTION OF THE INVENTION

Figure 1:
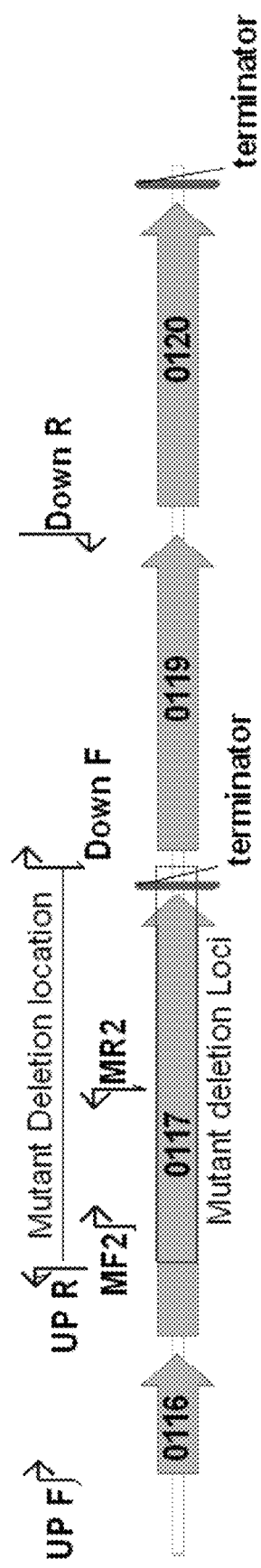
FIG. 1 depicts a portion of the genomic sequence of the wild type ZM4 strain, the location of the deleted portion in AcR, and the primers used in the experiments described in Example 1 and Example 2. 0116, 0117, 0119, and 0120 represent the genes, ZMO0116, ZMO0117, ZMO0119, and ZMO0120, respectively. The two "terminators" are terminator sited predicted by TIGR annotation. The grey line above the ORFs and the open ORF box without an arrow referred to as "Mutant Deletion location" is the genomic sequence present in wild type ZM4 but deleted in AcR mutant. UP_F, UP_R, Down_F, and Down_R are primers used for construction of the deletion mutant mimicking the AcR mutant with the 1.5-kb deletion using the pJK100 deletion system. MF2 and MR2 are primers used to construct the insertional mutant of ZMO0117 using the pKnock system. The primer sequences are: MF2: gtatcgacgtcaccggtctt (SEQ ID NO: 6); MR2: ggctccatcagacagttggt (SEQ ID NO: 7); UP_F: CGAGCTCtttcgtcgataaggaatcagc (SEQ ID NO: 8); UP_R: GCCGCGGcggaagtcaaccagatgata (SEQ ID NO: 9); Down_F: GCATATGCgatattagacaatagcttg (SEQ ID NO: 10); and Down_R: CGAATTCtatcgcagcaaaagccataa (SEQ ID NO: 11). Capitalized nucleotides represent a restriction enzyme site.

It has been identified in accordance with the present invention that increased expression of a sodium-proton antiporter gene in a microorganism confers enhanced acetate resistance to the microorganism. The present invention provides strains of microorganisms displaying enhanced resistance to acetate, which are particularly advantageous for use in fermentation of biomass materials to produce biofuels such as ethanol and butanol. The present invention also provides methods for producing such microbial strains, as well as related novel promoter sequences and expression vectors. Further, the present invention provides methods of producing biofuels from fermentation of biomass materials by utilizing the microorganisms of the present invention.

In one aspect, the invention is directed to isolated strains of microorganisms that display enhanced resistance to acetate as a result of increased expression of a sodium-proton antiporter in the microorganism.

In one embodiment, the sodium-proton antiporter being expressed at an elevated level is a plasma membrane sodium-proton antiporter. In other embodiments, the sodium-proton antiporter being expressed at an elevated level is a sodium-proton antiporter other than a plasma membrane sodium-proton antiporter; for example, an endosomal or vacuolar sodium-proton antiporter.

The sodium-proton antiporter being expressed at an elevated level is preferably encoded by an nhaA gene or an nhaA homolog.

The name "nhaA", as used herein and consistent with the understanding in the art, refers to a gene that encodes a plasma membrane sodium proton anti-porter in a microorganism. nhaA has been identified from a wide variety of microorganisms and the function of the encoded protein appears to be conserved based on significant sequence homologies shared across species. The nhaA gene and the encoded protein from the ZM4 strain of *Zymomonas mobilis* are described in FIGS. 4A-4B, and also set forth in SEQ ID NOS: 1 and 2, respectively. The *E. coli* nhaA gene (SEQ ID NO: 12) and the encoded Na$^+$/H$^+$ anti-porter protein (SEQ ID NO: 13) have been extensively characterized, as summarized in the EcoCyc™ database for the *Escherichia coli* K-12 MG1655, available online Na$^+$/H$^+$ anti-porter genes have also been identified from various yeast species. For example, the plasma membrane Na$^+$/H$^+$ anti-porter has been identified from *Schizosaccharomyces pombe* and named as "SOD2" (Jia et al. 1992). NHA1 has been cloned from *S. cerevisiae* (Prior et al. 1996). The nucleotide and amino acid sequences of *S. cerevisiae* NHA1 are set forth in SEQ ID NO: 14 and SEQ ID NO: 15, respectively.

For purpose of the present invention, the terms "nhaA" and "nhaA homolog" together include both microbial genes that have been named as nhaA, as well as genes that have been named differently (e.g., SOD2 or NHA1) and also encode a plasma membrane sodium proton anti-porter of a microorganism that can be readily determined to be the nhaA counterpart of that microorganism based on sequence comparison, plasma membrane localization and/or functional characteristics. For example, a gene that encodes a protein that shares at least 35% identity or similarity, or preferably 40%, 45%, 50%, 60%, 75%, or 85% identity or similarity, or more preferably 90% or 95% identity or similarity, with the protein sequence of SEQ ID NO: 2 (*Zymomonas mobilis*), SEQ ID NO: 13 (*E. coli*), or SEQ ID NO: 15 (*S. cereviasiae*), can be considered an nhaA gene or homolog. Similarity between two protein sequences can be determined, for example, using the well known Lipman-Pearson Protein Alignment program with the following choice of parameters: Ktuple=2, Gap Penalty=4, and Gap Length Penalty=12. Alternatively, a gene that shares at least 45% identity, or preferably 50%, 60%, 75%, or 85% identity, or more preferably 90% or 95% identity with the nucleotide sequence of SEQ ID NO: 1, SEQ ID NO: 12 (*E. coli*), or SEQ ID NO: 14 (*S. cereviasiae*), or a gene that hybridizes to a nucleic acid represented by any one of SEQ ID NO: 1, SEQ ID NO: 12, or SEQ ID NO: 14, or a full complement thereof, under stringent hybridization conditions, can be considered an nhaA gene or homolog. Appropriate hybridization conditions for such determination include hybridization at 42° C. to 65° C., followed by washing in 0.1× to 2×SSC, 0.1% SDS at a temperature ranging from room temperature to 65° C. More preferably but not absolutely necessary, the determination of whether a particular gene is nhaA or not is made in conjunction with confirmation that the encoded protein is localized in the plasma membrane and/or with a functional determination that the gene is involved in sodium proton exchange.

The term "nhaA homolog" also includes genes that encode a microbial sodium proton anti-porter that shares significant sequence homology to nhaA and is not necessarily a plasma membrane sodium proton anti-porter; for example, an endosomal sodium proton anti-porter, or a vacuolar sodium proton anti-porter. By "significant sequence homology", it is meant that the homolog gene encodes a protein that shares at least 35% identity or similarity, or preferably 45%, 50%, 60%, 75%, or 85% identity or similarity, or more preferably 90% or 95% identity or similarity with the protein sequence of SEQ ID NO: 2, SEQ ID NO: 13 or SEQ ID NO: 15; or alternatively, the homolog gene shares at least 45% identity, or preferably 50%, 60%, 75%, or 85% identity, or more preferably 90% or 95% identity with the nucleotide sequence of SEQ ID NO: 1, SEQ ID NO: 12 or SEQ ID NO: 14, or hybridizes to a nucleic acid represented by SEQ ID NO: 1, SEQ ID NO: 12 or SEQ ID NO: 14 or the full complement thereof under stringent hybridization conditions defined above.

In accordance with the present invention, either a full length antiporter or a functional or enzymatically active fragment thereof, can be expressed at an elevated level to achieve enhanced resistance to acetate. The term "functional fragment" or "enzymatically active fragment" means a polypeptide fragment of a sodium-proton antiporter which substantially retains the activity of the full-length protein. By "substantially" it is meant at least about 50%, 60%, 70%, 80%, 90% or more of the activity of the full-length protein is retained. Based on the domain characterizations of sodium-proton antiporters and substantial consensus conserved among species, those skilled in the art can readily identify and make functional fragments of a sodium-proton antiporter using various genetic engineering techniques known in the art. The activity of any partial protein of interest can be determined using, e.g., functional complementation analysis, well known in the art.

The microbial strains of the present invention display enhanced resistance to acetate as a result of increased expression of a sodium-proton antiporter. By "increased expression", it is meant that the level of either mRNA or protein or both of the sodium-proton antiporter is increased, preferably as a result of a genetic modification, as compared to the wild type or parental strain without the genetic modification. The extent of increase in expression contemplated by the present invention is at least 50%, or at least 100% (i.e., twice the level of parental strain), or more preferably at least four or five times, or even more preferably at least ten to fifteen times, the level of parental strain. It has been demonstrated by the present inventors that the mRNA level of nhaA in both stationary and exponentially growing cells of the *Z. mobilis* mutant AcR was more than sixteen (16) times the level in a wild type strain.

According to the present invention, increased expression of a sodium-proton antiporter in a microorganism, preferably a plasma membrane sodium-proton antiporter encoded by nhaA or homolog, confers enhanced resistance to acetate. By "resistance to acetate", it is meant resistance to acetate salts including, for example, one or more of sodium acetate, potassium acetate, and ammonium acetate, and/or resistance to acetic acid. Resistance of a strain to acetate can be determined by assessing the growth of the strain in media containing various concentrations of acetate (e.g., sodium acetate) or acetic acid. By "enhanced resistance" it is meant that a strain containing a desirable genetic modification resulting in increased antiporter expression is able to grow in media containing a higher concentration of acetate (e.g., sodium acetate) or acetic acid than the unmodified strain. For example, the concentration of sodium acetate or acetic acid that can be tolerated by the strain is increased by 15%, 20%, 30%, or 50% or higher. For instance, wild type *Z. mobilis* strain ZM4 and the mutant strain AcR both grow well in media containing 8 g/L or even 12 g/L sodium acetate or acetic acid. However, the difference between the two strains is substantial when grown in media containing 16 g/L sodium acetate or acetic acid under anaerobic conditions. Alternatively, "enhanced resistance" can mean that the strain containing a genetic modification grows better than the unmodified strain in media containing a given concentration of sodium acetate or acetic acid, as measured by a shorter doubling time (e.g., shortened by 10%, 20%, 30% or 50% or greater) or a higher cell density reached at the end of the exponential growth phase (e.g., 25%, 50%, 75%, 100%, 150%, 200%, 500%, or even 1000% or higher cell density).

Microorganisms encompassed within the scope of the present invention include both bacteria and fungi.

In accordance with the present invention, bacterial strains having enhanced resistance to sodium acetate as a result of increased expression of nhaA include both Gram-positive and Gram-negative bacteria. Examples of Gram-positive bacteria include those from the genus of phylum Firmicutes, particularly strains of *Acetobacterium, Bacillus, Streptococcus*, and *Clostridium*. Examples of Gram-negative bacteria of particular interest include those generally considered medically safe, such as *Zymomonas* sp. (e.g., *Z. mobilis*), *Gluconobacter* sp. (e.g., *Gluconobacter oxydans*, previously known as *Acetobacter suboxydans*), Cyanobacteria, Green sulfur and Green non-sulfur bacteria. The acetate tolerant *Z. mobilis* mutant AcR described by Joachimstahl (1998) and derivatives made from this mutant (e.g., by further transformation with additional vectors in the same genetic background as the AcR mutant) are excluded from the scope of this invention. The term "same genetic background as the AcR mutant", as used in the context of the present invention, refers to strains bearing the same genetic modification as the AcR mutant which is responsible for the phenotype of enhanced resistance to acetate.

Fungal strains having enhanced resistance to acetate as a result of increased expression of nhaA include filamentous and unicellular fungal species, particularly the species from the class of Ascomycota, for example, *Saccharomyces* sp., *Kluyveromyces* sp., *Pichia* sp., *Candida* sp., and *Schizosaccharomycetes* sp. Preferred fungal strains contemplated by the present invention are *S. cerevisiae, S. pombe*, and *Pichia pastoris*.

Strains of microorganisms that display enhanced resistance to acetate as a result of increased expression of a sodium-proton antiporter can be made using any of the known genetic engineering techniques.

In one embodiment, a microbial strain having enhanced resistance to acetate can be created by genetically modifying the 5' upstream regulatory region of the endogenous nhaA gene of the strain.

It has been specifically demonstrated by the present inventors that a deletion of a 5' upstream sequence relative to the nhaA coding sequence in *Z. mobilis* results in an increased nhaA gene expression and enhanced resistance to acetate. More specifically, of the 158 nucleotides (SEQ ID NO: 3) of the nhaA promoter region, a deletion of the first 98 nucleotides (SEQ ID NO: 4), namely, the presence of the remaining 60 nucleotides (SEQ ID NO: 5), is sufficient to result in increased nhaA expression and enhanced acetate resistance.

In this context, the invention provides separate embodiments directed to isolated nucleic acids based on the 5' upstream regulatory elements (i.e., SEQ ID NO: 4 and 5) of the nhaA gene from *Z. mobilis*. Nucleic acid molecules derived from these specific elements, e.g., by substitution, addition or deletion of one or more nucleotides of SEQ ID NO: 4 or 5, are also contemplated by the present invention, so long as the modifications do not abolish the regulatory activity of SEQ ID NO: 4 or SEQ ID NO: 5. Those skilled in the art can further determine the minimal or critical element(s) within SEQ ID NO: 5 sufficient to direct elevated nhaA expression. Additionally, those skilled in the art can determine the regulatory element(s) within SEQ ID NO: 4, apparent responsible for negatively regulating the nhaA expression. A variety of methods and techniques are available for these determinations. For example, primer extension experiment can be conducted to determine the precise transcription start site. Promoter serial deletions can be generated and tested to identify the minimum sequence required for elevated nhaA expression. DNaseI footprint analysis can also be performed in order to identify potential repressor and activator sites within the promoter region. These regulatory elements identified in accordance with the present invention can be used independently, e.g., placed in operable linkage to a heterologous gene (a non-nhaA gene) for directing expression of such heterologous gene.

By modifying the 5' upstream region of the nhaA gene through, e.g., deletion of the first 98 nucleotides in the promoter sequence, the present invention provides a genetically modified Z. mobilis strain, wherein the modified promoter is characterized by SEQ ID NO: 5 (60 bp). Although the genetic modification of the 5' upstream region can include sequences of ORF 0117 (i.e., the ORF 5' of the nhaA promoter), the modifications contemplated by the present invention do not include the precise modification (i.e., 1.5 kb deletion) found in the AcR mutant. The genetic modification can include, however, a deletion of a 5' upstream sequence of less than 1.0 kb, or less than 500 bp, or less than 200 bp, or about 100 bp, which deletion includes at least the deletion of the 98 bp set forth in SEQ ID NO: 4, while preferably leaving the last 60 bp (SEQ ID NO: 5) of the promoter intact.

In another embodiment, a microbial strain having enhanced resistance to acetate can be created by introducing an exogenous expression vector into the strain which directs expression (i.e., additional expression) of a sodium-proton antiporter.

In a specific embodiment, the expression vector introduced into the strain expresses a plasma membrane sodium-proton antiporter. In a preferred embodiment, the sodium-proton antiporter is encoded by an nhaA gene. In an especially preferred embodiment, the sodium-proton antiporter is encoded by an endogenous nhaA gene (i.e., an nhaA gene native to the recipient strain), even though nhaA homologs from other related species can also be introduced.

Generally, the nhaA gene is placed in an operably linkage to a promoter and a 3' termination sequence that are functional in a recipient microbial host. The promoter can be a constitutive promoter or an inducible promoter. The promoter can be a native promoter (thereby the expression vector simply introducing additional copy or copies of the nhaA expression units) or a modified promoter derived from a native promoter (such as SEQ ID NO: 5), or a heterologous promoter from a different gene. Promoters suitable for use in expression of nhaA in a bacterial host include, for example, lac promoter, T7, T3 and SP6 phage RNA polymerase promoters. Specific examples of promoters suitable for use in expression in Zymomonas species include Z. mobilis pdc promoter and adhB promtoer. Specific examples of promoters suitable for use in expression in S. cerevisiae include adh1+ (constitutive high expression), fbp1+ (carbon source responsive), a tetracycline-repressible system based on the CaMV promoter, and the nmt1+ (no message in thiamine) promoter, which may be suitable for use in expression of nhaA in a yeast strain. The above examples of promoters are well documented in the art.

A variety of vector backbones can be used for purpose of the present invention. Choices of vectors suitable for transformation and expression in bacteria and fungi have been well documented in the art. For example, numerous plasmids have been reported for transformation and expression in Zymomonas, including, e.g., pZB serial plasmids developed based on Zymomonas cryptic plasmid, as described in U.S. Pat. Nos. 5,712,133, 5,726,053, and 5,843,760, and a cloning-compatible broad-host-range destination vector described by Pelletier et al. (2008), among many others.

The expression vector can include, in addition to the nhaA expression cassette, other sequences appropriate for maintenance and selection of the vector, e.g., a selection marker gene and a replication origin. The selection marker gene can be a gene that confers resistance to antibiotics such as ampicillin resistance (Amp$^r$), tetracycline resistance (Tet$^r$), neomycin resistance, hygromycin resistance, and zeocin resistance (Zeo$^r$) genes, or a gene that provides selection based on media supplement and nutrition.

The vector can be a replicative vector (such as a replicating circular plasmid), or an integrative vector which mediates the introduction of a genetic sequence into a recipient cell and subsequent integration of the sequence into the host genome.

An expression vector containing an nhaA expression cassette can be introduced into a microbial host by various approaches known in the art, including transformation (e.g., chemical reagent based transformation), electroporation and conjugation.

The genetically modified strains of microorganisms that display enhanced resistance to acetate as a result of increased expression of a sodium-proton antiporter can be additionally modified as appropriate. For example, Z. mobilis strains over-expressing nhaA can be additionally modified in order to expand the range of substrates that can be utilized by the strains for efficient ethanol production. For instance, Z. mobilis strains over-expressing nhaA can also be introduced with additional genes so that the strains can ferment xylose, arabinose or other pentose sugars as the sole carbon source to produce ethanol. See, e.g., U.S. Pat. No. 5,514,583. Additionally, yeast strains over-expressing NHA1 can be further modified to express xylose reductase, xylitol dehydrogenase and xylulokinase, and to have reduced expression of PHO13 or a PHO13 ortholog, in order to ferment xylose. See, e.g., U.S. Pat. No. 7,285,403.

The isolated or genetically modified microbial strains of the present invention are particularly useful for production of biofuels based on fermentation of biomass materials. Therefore, in a further aspect, the present invent provides a method of producing biofuels from cellulosic biomass based on use of the microbial strains of the present invention that are able to grow at elevated concentrations of acetate.

Biofuels contemplated by the present invention include particular the types of biologically produced fuels, such as bioalcohols, based on the action of microorganisms and enzymes through fermentation of biomass materials. Examples of bioalcohols include ethanol, butanol, and propanol.

In a typical cellulosic biomass to alcohol process, raw cellulosic biomass material is pretreated in order to convert, or partially convert, cellulosic and hemicellulosic components into enzymatically hydrolyzable components (e.g., poly- and oligo-saccharides). The pretreatment process also serves to separate the cellulosic and hemicellulosic components from solid lignin components also present in the raw cellulosic material. The pretreatment process typically involves reacting the raw cellulosic biomass material, often as a finely divided mixture or slurry in water, with an acid, such as sulfuric acid. Other common pretreatment processes include, for example, hot water treatment, wet oxidation, steam explosion, elevated temperature (e.g., boiling), alkali treatment and/or ammonia fiber explosion. The pretreated biomass is then treated by a saccharification step in which poly- and oligo-saccharides are enzymatically hydrolyzed into simple sugars. The free sugars and/or oligosaccharides produced in the saccharification step are then subjected to fermentation conditions for the production of ethanol or butanol, for example. Fermentation can be accomplished by combining one or more fermenting microorganisms with the produced sugars under conditions suitable for fermentation.

One can also add enzyme to the fermenter to aid in the degradation of substrates or to enhance alcohol production. For example, cellulase can be added to degrade cellulose to glucose simultaneously with the fermentation of glucose to ethanol by microorganisms in the same fermenter. Similarly, a hemicellulase can be added to degrade hemicellulose.

Because the pretreatment processes and by-products of fermentation can create a range of inhibitors including acetate, it is especially advantageous to utilize the genetically modified microbial strains described herein which display enhanced resistance to acetate and are able to continue fermentation despite acetate present in the fermentation broth, either in the fermentation substrate carried over from pretreatment of biomass material, or built up as a byproduct of fermentation.

For purpose of fermentation, one strain or a mixture of several strains, some or all of which display enhanced resistance to acetate, can be used.

Specific fermentation conditions can be determined by those skilled in the art, and may depend on the particular feedstock or substrates, the microorganisms chosen and the type of biofuel desired. For example, when *Zymomonas mobilis* is employed, the optimum pH conditions range from about 3.5 to about 7.5; substrate concentrations of up to about 25% (based on glucose), and even higher under certain conditions, may be used; and no oxygen is needed at any stage for microorganism survival. Agitation is not necessary but may enhance availability of substrate and diffusion of ethanol.

After fermentation, alcohol is separated from the fermentation broth by any of the many conventional techniques known to separate alcohol from aqueous solutions, including evaporation, distillation, solvent extraction and membrane separation. Particles of substrate or microorganisms may be removed before separation to enhance separation efficiency.

The present invention is further illustrated and by no means limited by the following examples.

Example 1

This example describes the materials and methods used in the experiments described in the subsequent examples.

Strains and Culture Conditions

Bacterial strains and plasmids used in this study are listed in Table 1. *E. coli* strains were cultured on Luria-Bertani (LB) broth or agar plates for cloning and strain maintenance. *Z. mobilis* ZM4 was obtained from the American Type Culture Collection (ATCC 31821). AcR is the *Z. mobilis* ZM4 acetate tolerant strain as described previously (Joachimstahl et al. 1998). ZM4 and AcR were cultured in RM medium at 30° C.

*S. cerevisiae* wild-type, deletion mutant and GST-fusion ORF over-expression strains were obtained through Open Biosystems (Huntsville, Ala.). *S. cerevisiae* strains were cultured in rich media (YPD media) and minimum complete medium (CM). CM media with 2% glucose was used for *S. cerevisiae* wild-type and *S. cerevisiae* deletion mutants. CM media with 2% glucose minus uracil was used for *S. cerevisiae* GST-over expressing strains, and 2% galactose was used to induce the GST-fusion strains.

The growth medium for *E. coli* WM3064 was supplemented with 100 µg/mL diaminopimelic acid (DAP). Plasmid-containing strains were routinely grown with antibiotics at the following concentrations (µg/mL): kanamycin of 50 for *E. coli* and 200 for ZM4; tetracycline, 10 for *E. coli* and 20 for ZM4; and gentamycin, 10 for *E. coli*, G418 of 200 for *S. cerevisiae* YKO deletion mutants.

PCR and DNA Manipulations

Genomic DNA from *Z. mobilis* was isolated using a Wizard Genomic DNA purification kit, following the manufacturer's instructions (Promega, Madison, Wis.). Purified DNA was quantified spectrophotometrically with NanoDrop 1000 System™ (Wilmington, Del.) as well as gel electrophoresis. The QIAprep Spin Miniprep™ kit and HiSpeed Plasmid Midi™ kit (Qiagen, Valencia, Calif.) were used for plasmid isolation. PCR, restriction enzyme digestion, ligation, cloning, and DNA manipulation were following essentially the standard molecular approaches.

Broad-Host-Range Destination Vector pBBR3DEST42 Construction

The construction of Gateway® cloning compatible broad-host-range destination plasmid vector pBBR3DEST42 was carried out as previously described (Pelletier et al. 2008), except that pBBRMCS-3 containing tetracycline resistance cassette was used herein instead of the previous construct pBBR5DEST42 from pBBRMCS-5 containing the gentamycin resistance cassette. Briefly, pBBR1MCS3 plasmid DNA digested with KpnI and PvuI was gel purified with Qiagen Gel purification kit (Qiagen, Valencia, Calif.) and treated with calf intestine alkaline phosphatase. The recombination region on pET-DEST42 vector DNA (Invitrogen, Carlsbad, Calif.) was PCR-amplified using the primers 42F and 42R that included KpnI and PvuI restriction sites. The gel-purified PCR product was ligated with pBBR1MCS3 KpnI/PvuI fragment with Fast-Link™ DNA Ligation Kit (Epicentre, Madison, Wis.). Ligation products were transformed into *E. coli* DB3.1 chemically competent cells (Invitrogen, Carlsbad, Calif.) and the transformants were selected by plating on LB agar plates containing tetracycline. Individual colonies were grown overnight in LB containing 30 µg/mL chloramphenicol and 10 µg/mL tetracycline, and plasmid DNA was prepared using QIAprep Spin Miniprep™ or HiSpeed Plasmid Midi™ kit following the manufacturer's protocol (Qiagen, Valencia, Calif.). Plasmid DNA was digested with KpnI and PvuI and digestion products were analyzed on an agarose gel to confirm the presence of products of the expected sizes.

ZMO0119 Gateway Entry Vector and Expression Clone Construction

The construction of entry vector and expression clone of target gene nhaA (ZMO0119) was carried out as described previously (Pelletier et al. 2008). Briefly, target gene nhaA (ZMO0119) was PCR amplified using AcR genomic DNA as template and primer nhaA_CF and nhaA_CR as primers. PCR products were then cloned into Gateway® entry clone pDONR221 using BP Clonase II enzyme mix following the manufacturer's protocol (Invitrogen, Carlsbad, Calif.), and then transformed into chemically competent DH5α cells (Invitrogen, Carlsbad, Calif.) and plated onto LB with appropriate antibiotic selection. The inserts were confirmed by sequencing using M13 forward and reverse primers (Integrated DNA Technologies, Inc., Coralville, Iowa). The confirmed entry clone vector was then recombined with the destination vector pBBR3DEST42 using LR Clonase II™ enzyme mix (Invitrogen Carlsbad, Calif.) to create the expression vector. The resulting expression vector construct was designed as p42-0119. The plasmid construct p42-0119 was confirmed by sequencing using BigDye Terminator v3.1 Cycle Sequencing Kit (Applied Biosystems Inc, Foster City, Calif.).

Mutant Plasmid Construction

For the insertional hcp mutant construction, the internal part of Z. mobilis hcp gene (ZMO0117) was amplified by PCR using MF2 and MR2 supplied by MWG-Biotech (Huntsville, Ala.). The hcp and nhaA gene as well as the primer positions used for mutant construction and nhaA gene-expressing vector are shown in FIG. 1. The 529-bp hcp internal part PCR product was then purified and cloned into pCR2.1-TOPO and then transformed into E. coli TOPO one competent cell (Invitrogen, Carlsbad, Calif.). The transformants with correct construct were confirmed by PCR and sequencing. The plasmid was then extracted using a Qiagen Midiprep™ kit and digested with XbaI and HindIII restriction enzymes, the 529-bp hcp internal part was then purified by Qiagen Gel purification kit. Similarly, pKnock-Km suicide vector was also digested with XbaI and HindIII restriction enzyme following by de-phosphorylation, and then ligated with 529-bp purified hcp internal part using Fast-Link™ DNA Ligation Kit (Epicentre, Madison, Wis.). The ligation product was then transformed into TransforMax EC100D pir-116 Electrocompetent E. coli competent cells (Epicentre, Madison, Wis.) by electroporation. The transformants containing plasmid pKm-0117 was selected on LB agar plate with 50 µg/mL kanamycin. The plasmid was then extracted from the transformant cells and the plasmid construct named as pKm-0117 was then sequenced to confirm the presence of the target gene fragment, which was then electroporated into E. coli WM3064 strain. The transformant E. coli WM3064 (pKm-0117) was verified by PCR and sequencing using BigDye Terminator v3.1 Cycle Sequencing Kit (Applied Biosystems Inc, Foster City, Calif.) for the presence of correct plasmid construct pKm-0117.

For the full deletion of most of the hcp gene and part of the nhaA gene promoter region to reconstruct the ZM4 wild-type strain to mimic the AcR strain 1.5-kb deletion region (See FIG. 1), the pJK100 plasmid was used for mutant plasmid construction as described previously (Denef et al. 2006). The primers used to amplify the upstream region (UP_F/UP_R) and downstream region (Down_F/Down_R) for mutant plasmid construction were listed in Table 1, which generated an 805 and 1050-bp PCR fragment. The final plasmid construct was named as pJK_hcp_nhaA.

Plasmid Transformation of Z. mobilis

Z. mobilis wild-type ZM4 and acetate tolerant strain AcR cultures were grown aerobically at 30° C. in RM, and E. coli WM3064 containing plasmid pKm-0117, pJK_hcp_nhaA, or p42-0119 cultures were grown at 37° C. in LB containing 100 µg/mL DAP and 10 µg/mL tetracycline to exponential phase. E. coli WM3064 cells containing plasmid pKm-0117, pJK_hcp_nhaA, or p42-0119 were washed with RM for three times by centrifugation at 13,000 rpm for 1 min and resuspended in RM. Different ratio of ZM4 cells with E. coli WM3064 (pKm-0117) cells, E. coli WM3064 (pJK_hcp_nhaA), E. coli WM3064 (p42-0119) cells were mixed in different ratio (1:3, 1:1, and 3:1) and plated onto RM agar plates with 100 µg/mL DAP and 10 µg/mL tetracycline for plasmid p42-0119 conjugation or 50 µg/mL kanamycin for plasmid pKm-0117 or pJK_hcp_nhaA conjugation. The cells were incubated at 30° C. overnight. Conjugants were selected by plating on RM agar plates containing 20 µg/mL tetracycline for p42-0119 plasmid conjugants or 200 µg/mL kanamycin for pKm-0117 or pJK_hcp_nhaA plasmid conjugants at 30° C. The conjugants were confirmed for the presence of correct plasmid constructs by PCR and sequencing using BigDye Terminator v3.1 Cycle Sequencing Kit (Applied Biosystems Inc, Foster City, Calif.).

Z. mobilis ZM4 Ultrafast Genomic Pyrosequencing

Ultrafast pyrosequencing using the Roche 454 Genome Sequencer FLX System (454 Life Sciences, Branford, Conn.) was carried on according to manufacturer's instructions, and the GS FLX shotgun DNA library preparation method manual (454 Life Sciences, Branford, Conn.). Briefly, for Z. mobilis ZM4 genome resequencing, shotgun DNA library was prepared using the mechanically sheared Z. mobilis ZM4 genomic DNA fragments with specific A and B adaptors blunt end ligated. After adaptor ligation, the fragments were denatured and clonally amplified via emulsion PCR generating millions of copies of template per bead. The DNA beads were then distributed into picoliter-sized wells on a fibre-optic slide (PicoTiterPlate™), along with a mixture of smaller beads coated with the enzymes required for the pyrosequencing reaction, including the firefly enzyme luciferase. The four DNA nucleotides were then flushed sequentially over the plate. Light signals released upon base incorporation were captured by a CCD camera, and the sequence of bases incorporated per well was stored as a read.

Long paired-end DNA library was prepared using the same genomic DNA for shot-gun DNA library preparation following the 454 GS FLX long paired end library preparation method manual (454 Life Sciences, Branford, Conn.). Long paired-end DNA library reads were used to build the original contigs and to assemble the contigs into scaffolds. Briefly, DNA was sheared into ~3 kb fragments using hydroshear (Genomic Solutions Inc., Ann Arbor, Mich.), EcoRI restriction sites were protected via methylation, and biotinlylated hairpin adaptors (containing an EcoRI site) were ligated to the fragment ends. The fragments were subjected to EcoRI digestion and circularized by ligation of the compatible ends, and subsequently randomly sheared. Biotinlyated linker containing fragments were isolated by streptavidin-affinity purification. These fragments were then subjected to the standard 454 sequencing on the GS FLX system.

Pyrosequencing Data Analysis and Access

GS reference Mapper, one application from 454 Genome Sequencer FLX software package 1.1.03 (454 Life Sciences, Branford, Conn.), was used to map the reads generated from GS sequencer application onto the Z. mobilis ZM4 reference genome (GenBank accession: AE008692) and reference plasmids Z. mobilis ZM4 plasmid 1 (GenBank accession: AY057845) as described in the GS FLX Data Analysis Software Manual (454 Life Sciences, Branford, Conn.). Sequence reads, contigs, and quality scores for nucleotide sequences and contigs were provided by 454 Life Science. High quality differences in which the identity frequency of all reads greater than 85% were used to change the genome sequence prior to final annotation. De novo Assembler, another application from 454 Genome Sequencer FLX software package was used to assemble the sequence reads into contigs. The contigs generated were then compared with ZM4 genome sequence and the plasmid sequence deposited in GenBank (AY05748). Contigs belong to plasmid sequence were aligned to the reference sequence and the contig gaps in original deposit were corrected, which gave a full-length plasmid sequence.

Microarray Transcriptomic RNA Profiling:

Overall design—Whole genome expression profiles of exponential and stationary phase cells were analyzed for the wild-type Zymomonas mobilis ZM4 and acetate tolerant mutant AcR under 12 g/L sodium acetate and same molar concentration of sodium chloride (8.55 g/L) control conditions.

Growth protocol—Z. mobilis ZM4 was obtained from the American Type Culture Collection (ATCC31821) and cultured in RM medium at 30° C. For the inoculum preparation a single colony of ZM4 was added to a test tube containing 5 ml RM broth and cultured aerobically at 30° C. until it reached late exponential or early stationary phase. A 1/100 dilution was added into the pre-warmed RM broth (10 ml culture into 1000 ml RM), which was then cultured aerobically at 30° C. with shaking at 150 rpm for approximately 12 h. The optical density was measured with a spectrophotometer at $600_{nm}$ and the inoculum was added to each fermentor so that the initial $OD600_{nm}$ was approximately same in each fermentor. Batch fermentations were conducted in approximately 2.5 L of RM medium in 7.5-L BioFlo110 bioreactors (New Brunswick Scientific, Edison, N.J.) fitted with agitation, pH, temperature and DOT probes and controls. Culture pH was monitored using a pH electrode (Mettler-Toledo, Columbus, Ohio) and the pH control set point was maintained at 5.0 by automatic titration with 3 N KOH. Temperature was maintained automatically at 30° C. and the vented gases exiting fermentors were passed through condenser units, chilled by a NESLAB Merlin M-150 refrigerated recirculator (Thermo Fisher Scientific, Newington, N.H.) to a vented hood via a water trap. DOT was monitored by using InPro 6800 series polarographic $O_2$ sensors (Mettler-Toledo). Three anaerobic fermentors were sparged overnight with filter-sterilized $N_2$ gas and for approximately one hour post-inoculation and the three aerobic fermentors were continually sparged with filter-sterilized air at 2.5 L/min to maintain fully aerobic conditions. The agitation rate was 700 rpm in each vessel.

RNA extraction protocol—RNA was isolated essentially described previously [26]. Briefly, samples from aerobic and anaerobic fermentors were harvested by centrifugation and the TRIzol reagent (Invitrogen, Carlsbad, Calif.) was used to extract total cellular RNA. Each total RNA preparation was treated with RNase-free DNase I (Ambion, Austin, Tex.) to digest residual chromosomal DNA and subsequently purified with the Qiagen RNeasy Mini kit in accordance with the instructions from the manufacturer. Total cellular RNA was quantified at $OD_{260}$ and $OD_{280}$ with a NanoDrop™ ND-1000 spectrophotometer (NanoDrop Technologies, Wilmington, Del.). The purified RNA from each sample was used as the template to generate ds-cDNA using Invitrogen ds-cDNA synthesis kit (Invitrogen, CA).

Label, hybridization, and scan protocol: The ds-cDNA was sent to NimbleGen for labelling, hybridization, and scanning following company's protocols.

Bioscreen Assay

Growth was monitored turbidometrically by measuring optical density at 600 nm intermittently with Bioscreen C Automated Microbiology Growth Curve Analysis System (Growth Curve USA, Piscataway, N.J.). For the inoculum preparation, a single colony of ZM4 was added to a test tube containing 5 ml RM (pH5.0) broth and cultured aerobically at 30° C. until it reached exponential phase. Twenty-μL culture was then transferred into 250-μL RM media in the Bioscreen C plate. The growth differences of different strains were monitored by Bioscreen C under both aerobic and anaerobic conditions in RM (pH5.0). Each experiment has been repeated at least three times. Replicates were used for each condition.

TABLE 1

Bacterial strains, plasmids and primers used in this application

| Strain, plasmid, or primer | Genotype, phenotype, or sequence of primer (5' to 3') | Reference |
|---|---|---|
| *E. coli* | | |
| K-12 | K-12 MG1655 Wild-type strain | Joachimstahl et al. (1998) |
| DH5α | F⁻ φ80dlacZΔM15 Δ(lacZYA-argF) U169 recA1 endA1 hsdR17($r_k^-$, $m_k^+$)phoA supE44 λ⁻ thi-1 gyrA96 relA1 | Novagen |
| DB3.1 | F⁻ gyrA462 endA1Δ(sr1-recA) mcrB mrr hsdS20($r_B^-$, $m_B^-$) supE44 ara-14 galK2 lacY1 proA2 rpsL20(Sm$^R$)xyl-5λ-leu mtl1 | Invitrogen |
| WM3064 | | Denef et al. (2006) |
| BL21(DE3) | F-ompT hsdSB(rB-mB-) gal dcm (DE3) | Invitrogen |
| *Zymomonas mobilis* | | |
| ZM4 | ATCC31821 | |
| AcR | ZM4 acetate tolerant strain generated by random mutagenesis | Joachimstahl et al. (1998) |
| ZM4(p42-0119) | ZM4 containing plasmid p42-0117 | This application |
| ZM4IM0117 | Insertional mutant of ZM4 gene ZMO0117 | This application |
| ZM4DM0117 | Deletion mutant of ZM4 gene ZMO0117 and part of ZMO0119 promoter region to mimic the AcR deletion region | This application |
| *S. cerevisiae* | | |
| BY4741 | MATa his3Δ1 leu2Δ0 ura3Δ0 met15Δ0-s288c background | Open Biosystems |
| YSC1021-552692 | Yeast: Yeast Knock Out Strain, NHA1 Clone Id: 4095 Accession: YLR138W | Open Biosystems |
| YSC1021-551633 | Yeast: Yeast Knock Out Strain, VNX1 Clone Id: 1123 Accession: YNL321W | Open Biosystems |
| YSC1021-555633 | Yeast: Yeast Knock Out Strain, NHX1 Clone Id: 4290 Accession: YDR456W | Open Biosystems |

TABLE 1-continued

Bacterial strains, plasmids and primers used in this application

| Strain, plasmid, or primer | Genotype, phenotype, or sequence of primer (5' to 3') | Reference |
|---|---|---|
| YSC1021-551268 | Yeast: Yeast Knock Out Strain, PSR1 Clone Id: 1498 Accession: YLL010C | Open Biosystems |
| YSC4515-98809240 | Yeast GST-Tagged Strain, NHA1 Clone Id: YLR138W Accession: YLR138W | Open Biosystems |
| YSC4515-98810980 | Yeast GST-Tagged Strain, PSR1 Clone Id: YLL010C Accession: YLL010C | Open Biosystems |
| Plasmids | | |
| pKNOCK-Km | $Km^r$, mob, broad host range cloning vector, 1.8 kb | Alexeyev et al. (1999) |
| pJk100 | $Km^r$, mob, broad host range suicide vector | Denef et al. (2006) |
| pET-DEST42 | $Ap^r$, $Cm^r$, C-terminal 6 × His and V5 epitope | Invitrogen |
| pBBR1MCS-3 | $Tc^r$, mob, broad host range cloning vector | |
| pBBR3DEST42 | $Cm^r$ $Tc^r$, C-terminal 6 × His and V5 epitope | This application |
| pDONR221 | $Km^r$, gateway entry vector $Gm^r$, N-terminal GST | Invitrogen |
| p42-0119 | pBBR3DEST42 containing ZM4 gene ZMO0119 | This application |
| Primers | | |
| MF2 | gtatcgacgtcaccggtctt (SEQ ID NO: 6) | 529-bp |
| MR2 | ggctccatcagacagttggt (SEQ ID NO: 7) | |
| UP_F | CGAGCTCtttcgtcgataaggaatcagc (SEQ ID NO: 8) | 805-bp |
| UP_R | GCCGCGGcggaagtcaaccagatgata (SEQ ID NO: 9) | |
| Down_F | GCATATGCgatattagacaatagcttg (SEQ ID NO: 10) | 1205-bp |
| Down_R | CGAATTCtatcgcagcaaaagccataa (SEQ ID NO: 11) | |

Example 2

This example describes the results from the experiments conducted to determine the genetic basis for the acetate tolerance observed with the mutant Z. mobilis strain, AcR.

Figure 2:
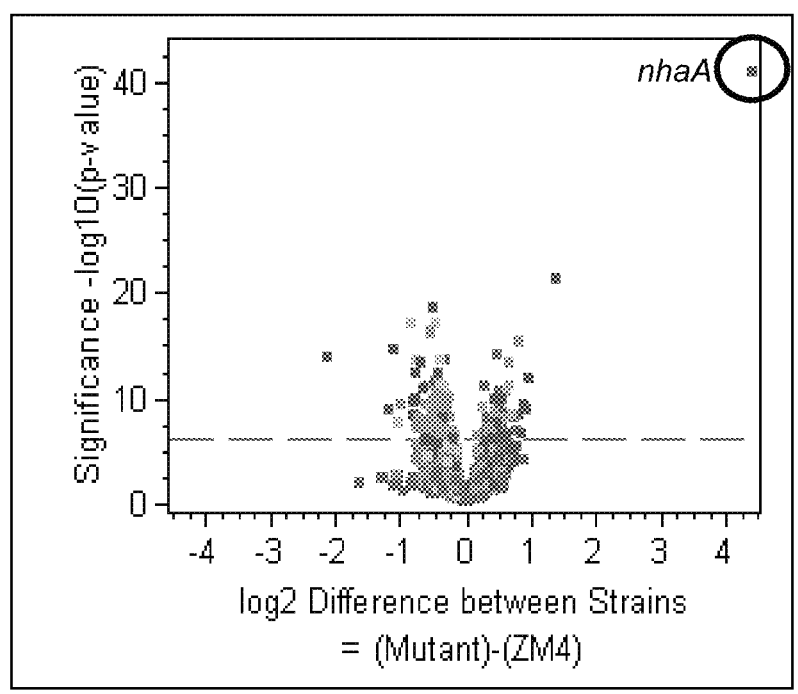
FIG. 2 depicts the Volcano plot results from a JMP Genomics microarray analysis showing a summary of all significantly differentially expressed genes between AcR and the ZM 4 wild-type strain for all conditions (sodium acetate and sodium chloride in exponentially and stationary phase cells). The X-axis shows the difference values between AcR and ZM4 expression profiles based on a $\log_2$ scale. The Y-axis shows statistical significance values for expression values, based on a $-\log_{10}$ p-value. The dashed line shows the statistical significance cut-off used in this study.

Using microarray comparative genome sequencing, next generation 454-pyroresequencing, and Sanger sequencing approaches, it was identified and confirmed that the genomic differences between the wild-type Z. mobilis strain, ZM4, and the acetate mutant AcR strain. The genetic changes in the mutant included a 1.5-kb deletion (FIG. 1) and single nucleotide polymorphisms (SNPs). Expression of the nhaA sodium proton anti-porter gene in AcR was found to be constitutive and significantly higher than in the wild-type strain under all the conditions tested (FIG. 2). Whole genome expression profiles were analyzed for mutant and wild-type exponential and stationary phase cells under sodium acetate and sodium chloride control conditions. A summary of these data is presented in FIG. 2 and Table 2.

TABLE 2

Expression data related to the anti-porter ZMO0119 loci.

| | | Microarray | |
|---|---|---|---|
| Gene ID | Product | AcR_Exp/ ZM4_Exp | AcR_Stationary/ ZM4_Stationary |
| ZMO0117 | Hybrid cluster protein | −2.15 | −2.20 |
| ZMO0119 | Na+/H+ antiporter NhaA (NhaA) | 4.60 | 4.27 |
| ZMO0120 | Dihydroorotate dehydrogenase | 1.71 | 0.97 |

AcR_Exp/ZM4_Exp: the ratio of gene expression between acetate tolerant mutant AcR in exponential phase and wild-type ZM4 in exponential phase;
AcR_Stationary/ZM4_Stationary: the ratio of gene expression between acetate tolerant mutant AcR in stationary phase and wild-type ZM4 in stationary phase.
The numbers are log2 based.

Example 3

This example describes experiments conducted to test the hypothesis that the 1.5-kb deletion in the AcR genome resulted in increased nhaA expression that conferred increased acetate tolerance in the mutant.

Figure 3:
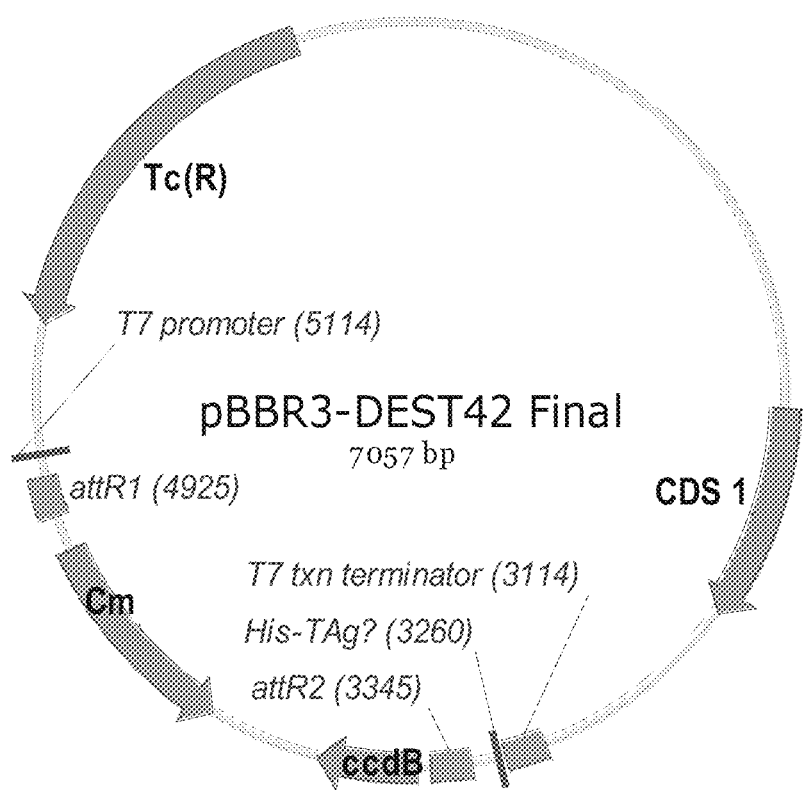
FIG. 3 graphically depicts the vector map of plasmid pBBR3-DEST42 constructed to analyze gene over-expressing and complementation. Tc(R): Tetracycline resistance gene tet; Cm: chloramphenicol resistance gene cat. attR1 and attR2 are recombination sites allowing recombinational cloning of the gene of interest from an entry clone; ccdB is ccdB gene allowing negative selection of expression clones.

A new Gateway® cloning compatible vector pBBR3-DEST42 was constructed. This vector contained the tetracycline resistance gene (FIG. 3) for candidate gene over-expression in ZM4 due to intrinsic, broad Z. mobilis antibiotic resistance. The anti-porter nhaA gene (FIG. 4) was cloned into the vector resulting in a nhaA over-expression vector p42-0119, which was then transformed into the wild-type ZM4 strain through conjugation to generate a strain over-expressing nhaA, which was named as "ZM4(p42-0119)". In addition, a deletion mutant was constructed to mimic the 1.5-kb deletion region (FIG. 1) of the AcR acetate tolerant strain using the pJK100 system (Denef et al. 2006). Since the deletion covers most of the hypothetical protein ZMO0117 and the promoter region of ZMO0119 (nhaA) gene (FIG. 1), an insertional mutant of ZMO0117 was created using the pKNOCK system (Alexeyev 1999) to investigate the relationship between gene ZMO0117 and acetate tolerance.

Figure 5A:
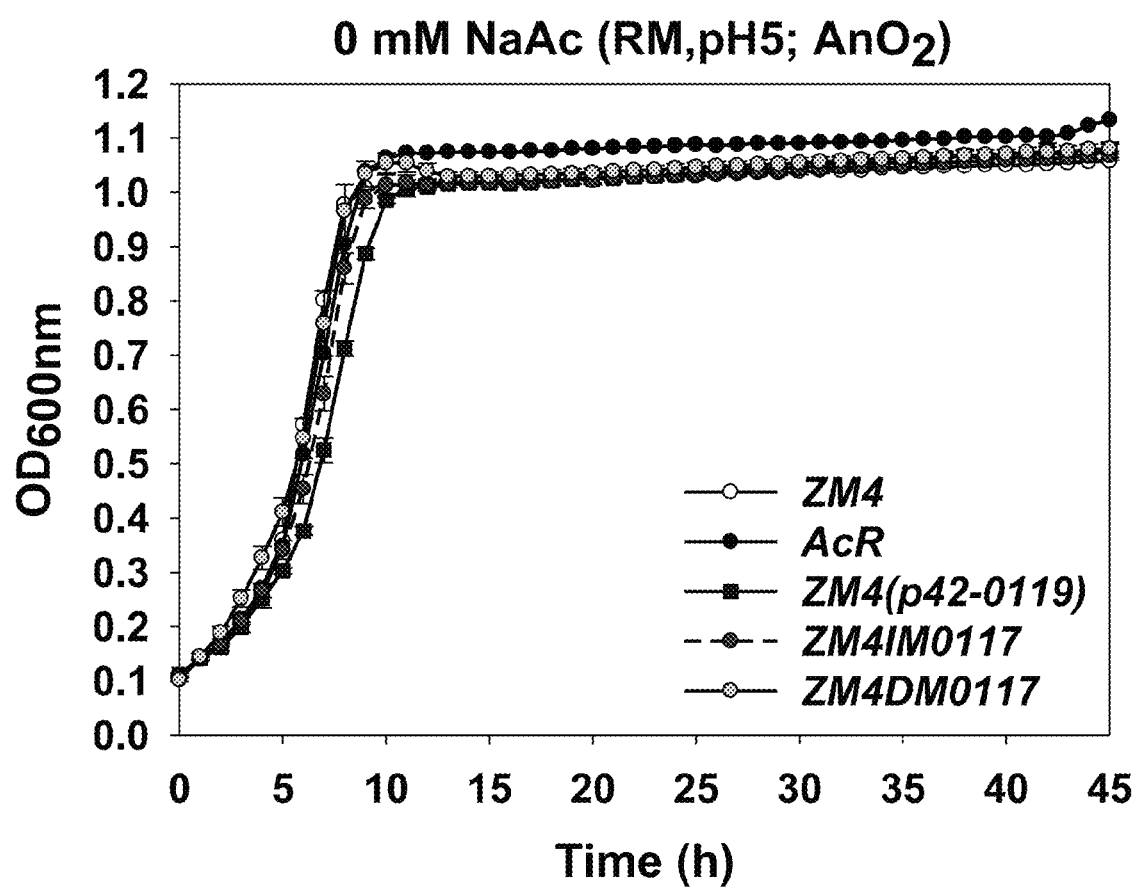
FIGS. 5A-5F. The strains were grown in RM (pH5.0) overnight, and a 20-1 μL culture was then transferred into 250-1 μL RM media in the Bioscreen plate. The growth of all strains was monitored by Bioscreen (Growth Curve USA, Piscataway, N.J.) under anaerobic (A, B, C) and aerobic (D, E, F) conditions in RM (pH5.0) containing 0 g/L NaAc (A, D), 12 g/L NaAc (B, E), and 16 g/L NaAc (C, F) respectively. The strains included in this study are: ZM4: *Zymomonas mobilis* ZM4 wild-type; AcR: ZM4 acetate tolerant mutant; ZM4 (p42-0119): ZM4 containing a gateway plasmid p42-0119 over-expressing ZM4 gene ZMO0119; ZM4IM0117: ZM4 insertional mutant of ZMO0117; ZM4DM0117: ZM4 deletion mutant mimicking AcR strain with a 1.5-kb deletion affecting ZMO0117 and the promoter region of ZMO0119. This experiment was repeated at least three times with similar results. Triplicates were used for each condition.
Figure 5B:
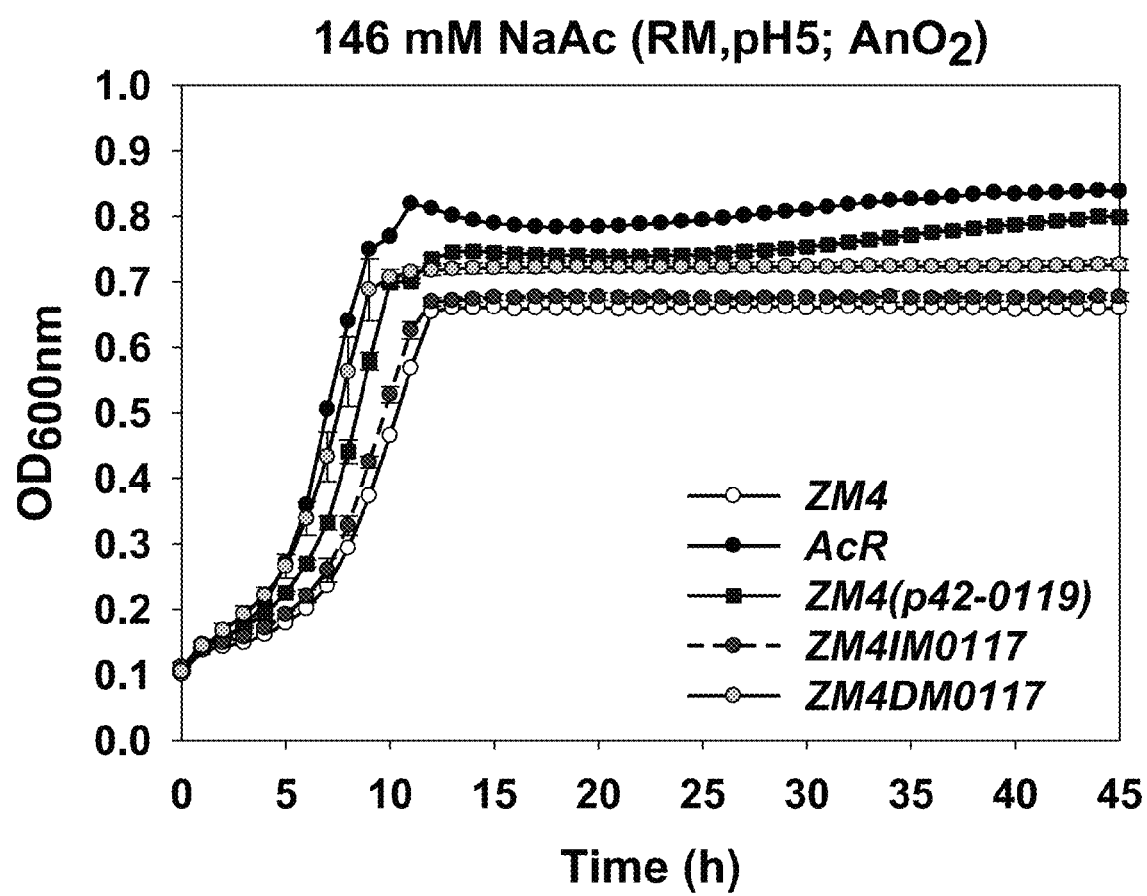
Figure 5C:
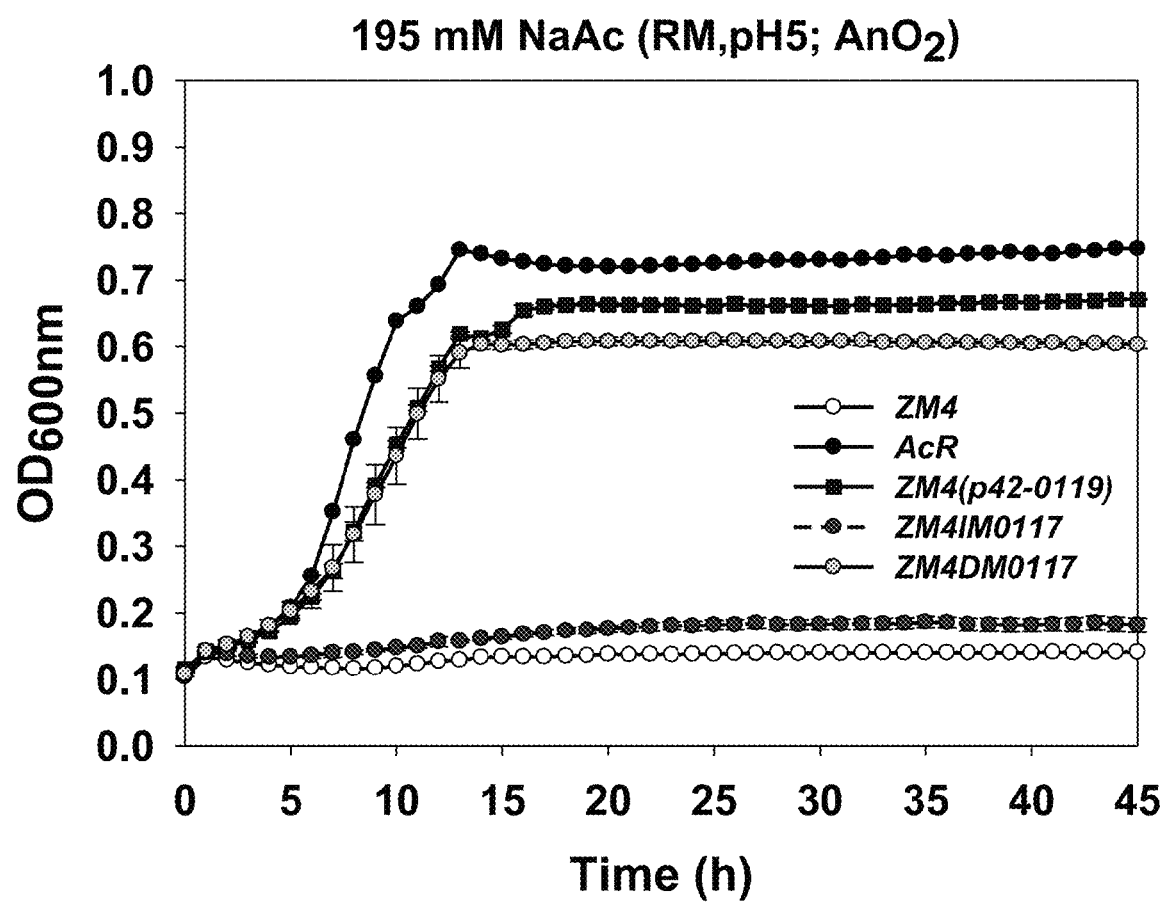
Figure 5D:
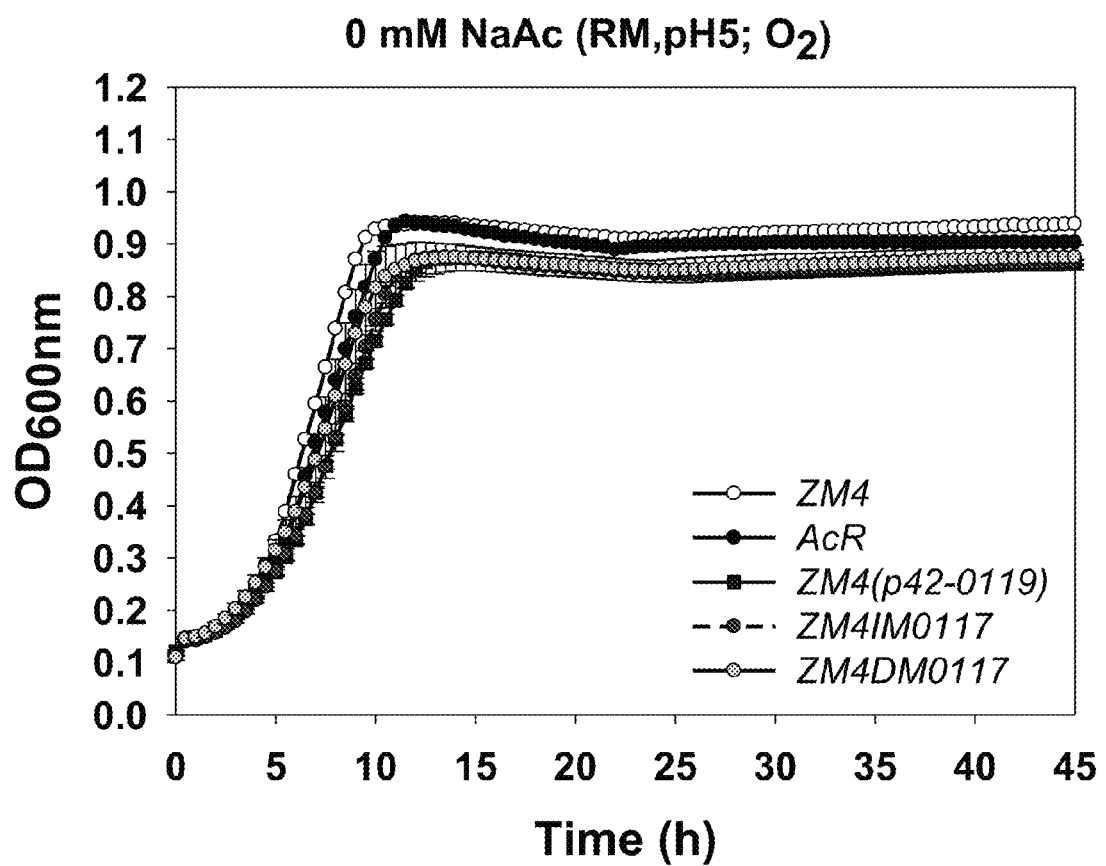
Figure 5E:
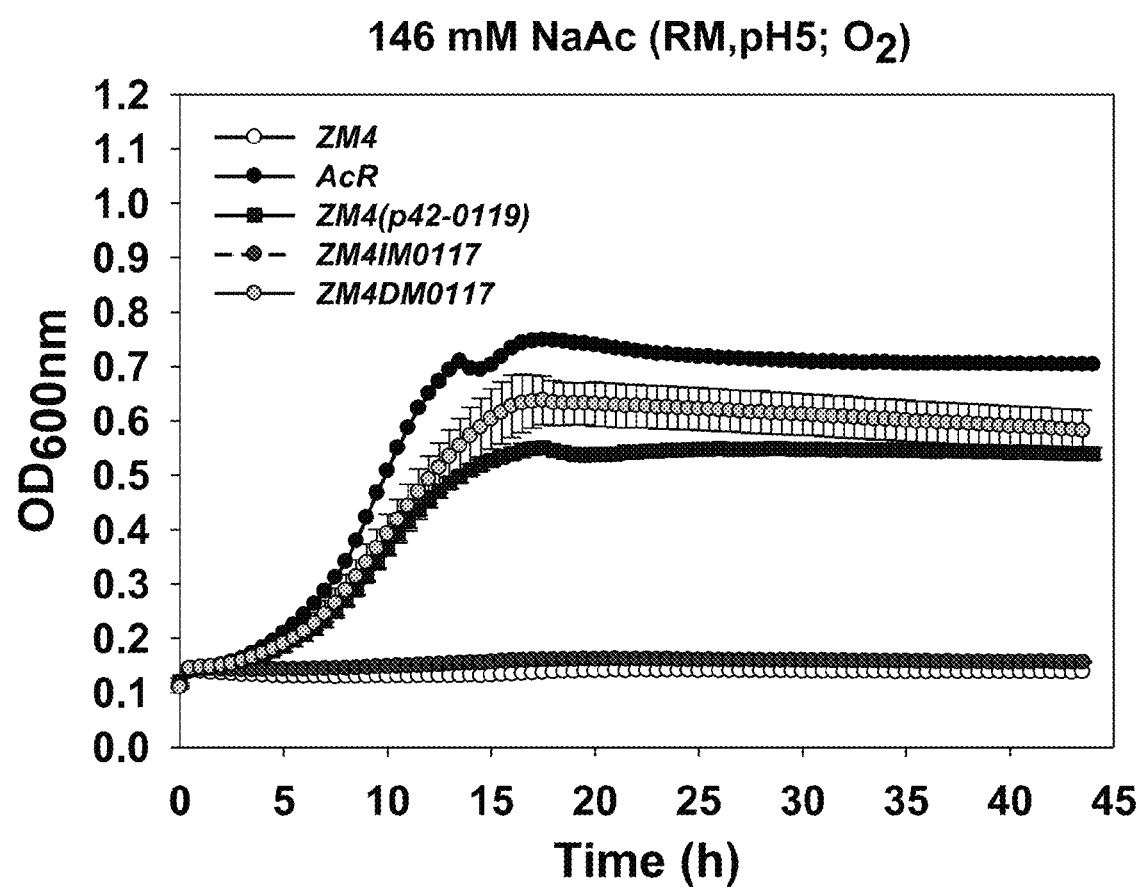
Figure 5F:
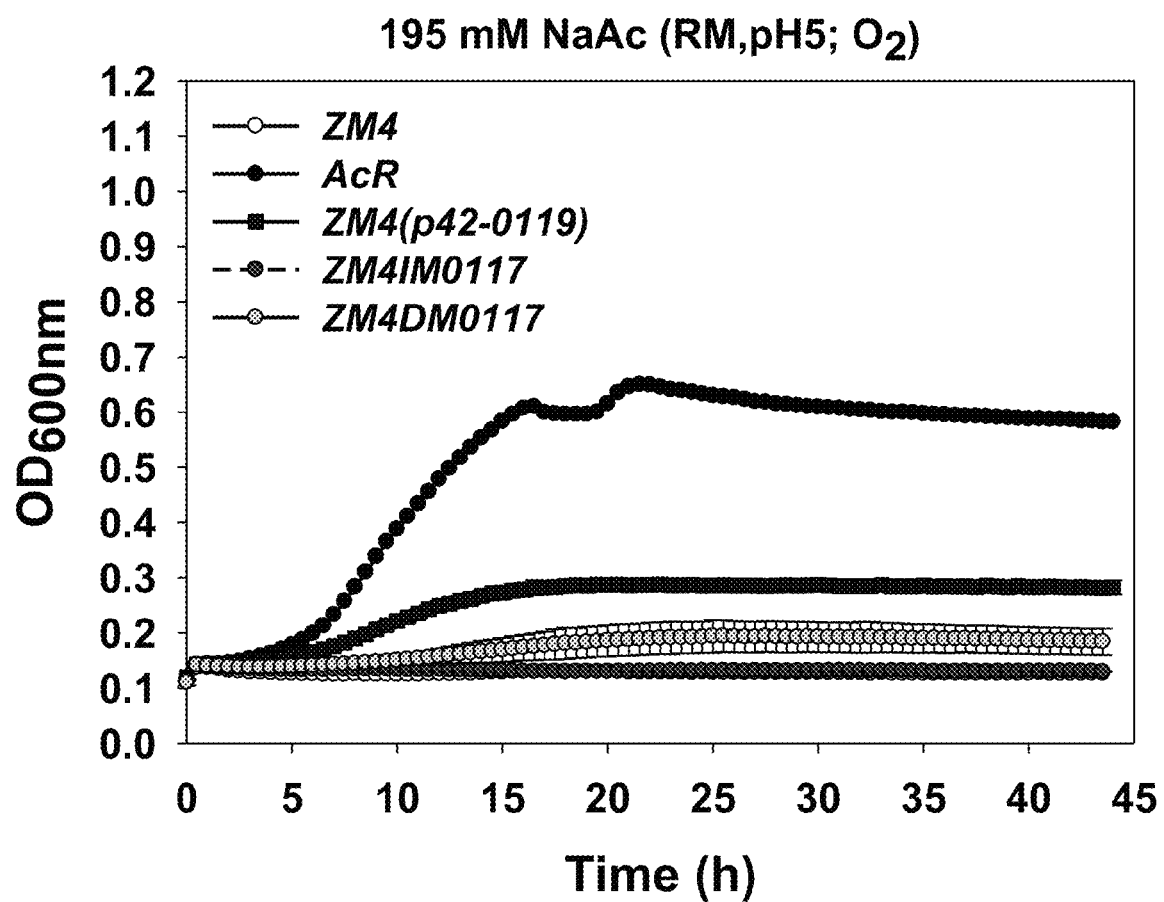
Figure 6:
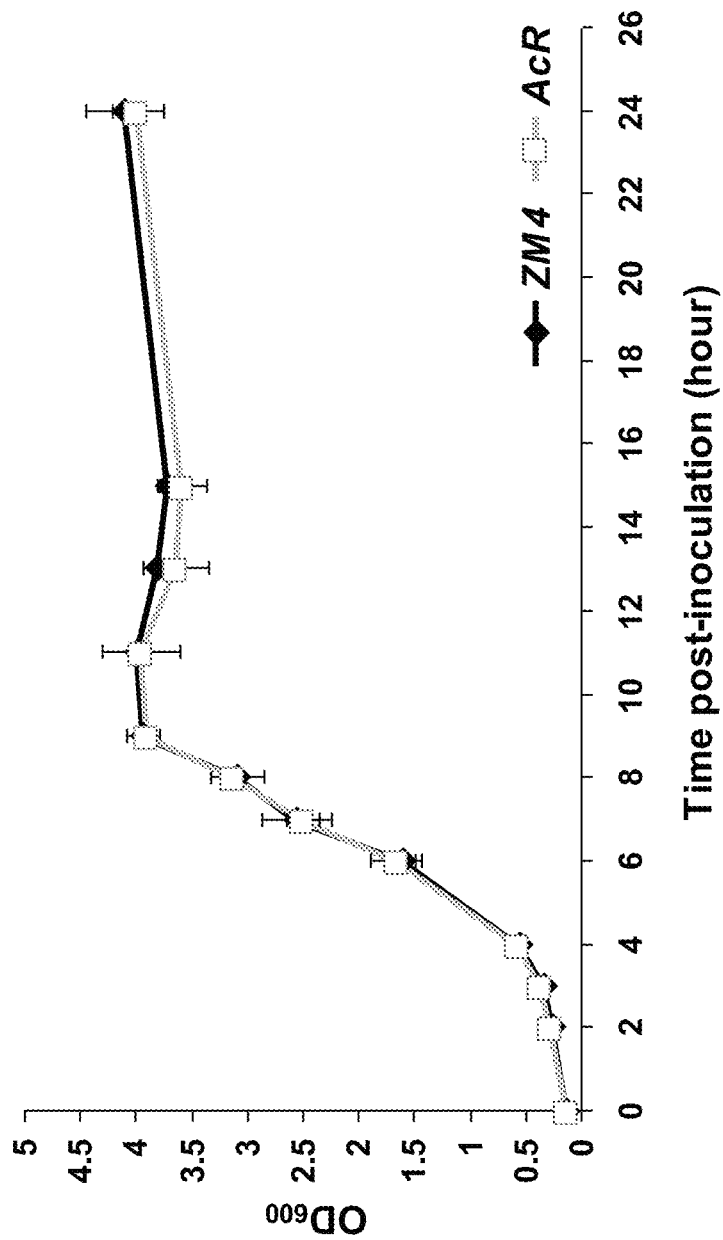
FIG. 6 shows the growth curve of wild-type *Z. mobilis* ZM4 and acetate tolerant mutant AcR in RM with 8.55 g/L NaCl. The data are from well-controlled anaerobic fermentation. The average of two replicate fermentors for each strain was plotted against the time post-inoculation with the bar showing the standard deviation.

The wild-type ZM4 strain, the acetate mutant AcR, the 1.5-kb deletion mutant ZM4DM0117, the insertional mutant ZM4IM0117, and the nhaA over-expression strain ZM4(p42-0119) were used in a BIOSCREEN C™ automated microbiology growth curve analysis system to test their susceptibilities to sodium acetate stress. All strains grew similarly under anaerobic and aerobic condition in the absence of sodium acetate (FIGS. 5A and 5D). However, in the presence of 12 g/L (146 mM) sodium acetate, ZM4 wild-type and the ZM4IM0117 grew more slowly, but ZM4DM0117 and ZM4 (p42-0119) were more resistant to sodium acetate stress (FIG. 5B) under anaerobic conditions. The ZM4 wild-type strain and acetate tolerant mutant AcR grew similarly with the presence of same molar amount of sodium ion (8.6 g/L sodium chloride), which indicated that nhaA was responsible for acetate tolerance of AcR (FIG. 6). The difference was more dramatic when the sodium acetate concentration was increased to 16 g/L (196 mM), with the growth of both ZM4 and ZM4IM0117 almost completely inhibited, while ZM4DM0117 and ZM4(p42-0119) were able to grow well (FIG. 5C). Stressors other than sodium acetate, such as reactive oxygen species and toxic end-products, may be present under aerobic conditions (Yang et al. 2009) and over-expression of nhaA also aided the ability of ZM4 to grow under these conditions although at lowers concentrations than during that of anaerobic growth. For example, ZM4 wild-type and ZM4IM0117 grew very poorly or not at all in the presence of 12 g/L sodium acetate while strains ZM4DM0117 and ZM4 (p42-0119) grew well (FIG. 5E).

These results indicate that over-expression of the nhaA gene in ZM4 rendered ZM4 tolerant to sodium acetate, and gene ZMO0117 was not responsible for the sodium acetate tolerance.

The promoter sequence (158-bp) of the nhaA gene in the wild type ZM4 strain is:

(SEQ ID NO: 3)
Tagagtcaaagagtttaattattttacggggaagggggctttggctcc cctttctgtattcatgaaagaggcggttttatatcaaaaagagggcg atattagacaatagcttggtttgattttagctatacgtttgatcaataa ggcaggat.

The portion of the nhaA promoter having been deleted in the AcR mutant (98-bp):

(SEQ ID NO: 4)
Tagagtcaaagagtttaattattttacggggaagggggctttggctcc cctttctgtattcatgaaagaggcggttttatatcaaaaagaggg.

The promoter sequence of nhaA remaining in AcR (60-bp):

(SEQ ID NO: 5)
cgatattagacaatagcttggtttgattttagctatacgtttgatcaat aaggcaggat.

Example 4

This example describes experiments conducted to investigate the role of nhaA on different forms of acetate.

Figure 7A:
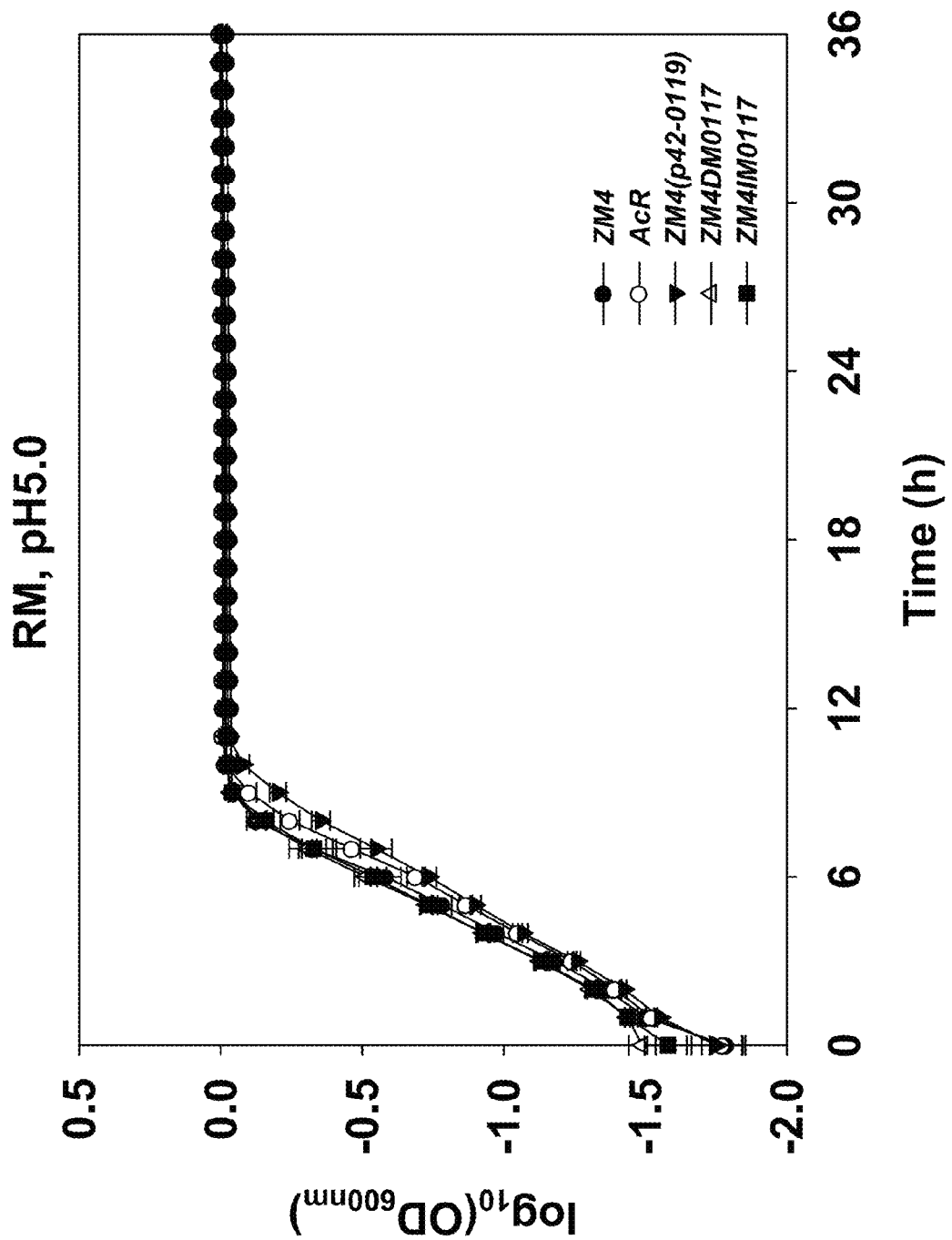
FIGS. 7A-7C show the effect of nhaA on growth of *Z. mobilis* in different forms of acetate. The growth differences of different strains were monitored by Bioscreen C (Growth Curves USA) under anaerobic conditions in RM, pH 5.0 (A); RM with 195 mM NaAc, pH 5.0 (B); 195 mM NaCl, NaAc, NH4OAc, or KAc at pH 5.0 (C). This experiment was repeated at least three times with similar results. Duplicates were used for each condition.
Figure 7B:
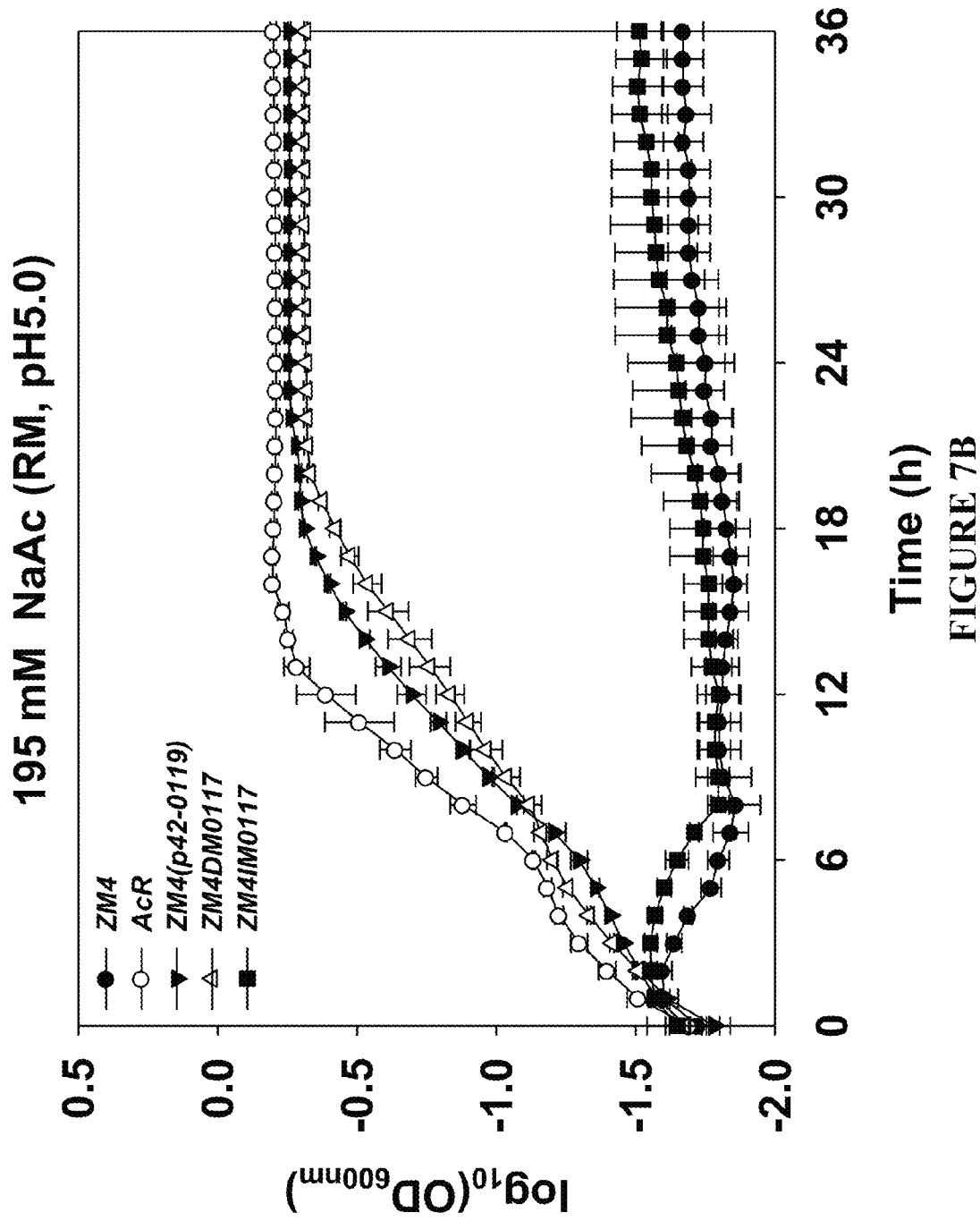
Figure 7C:
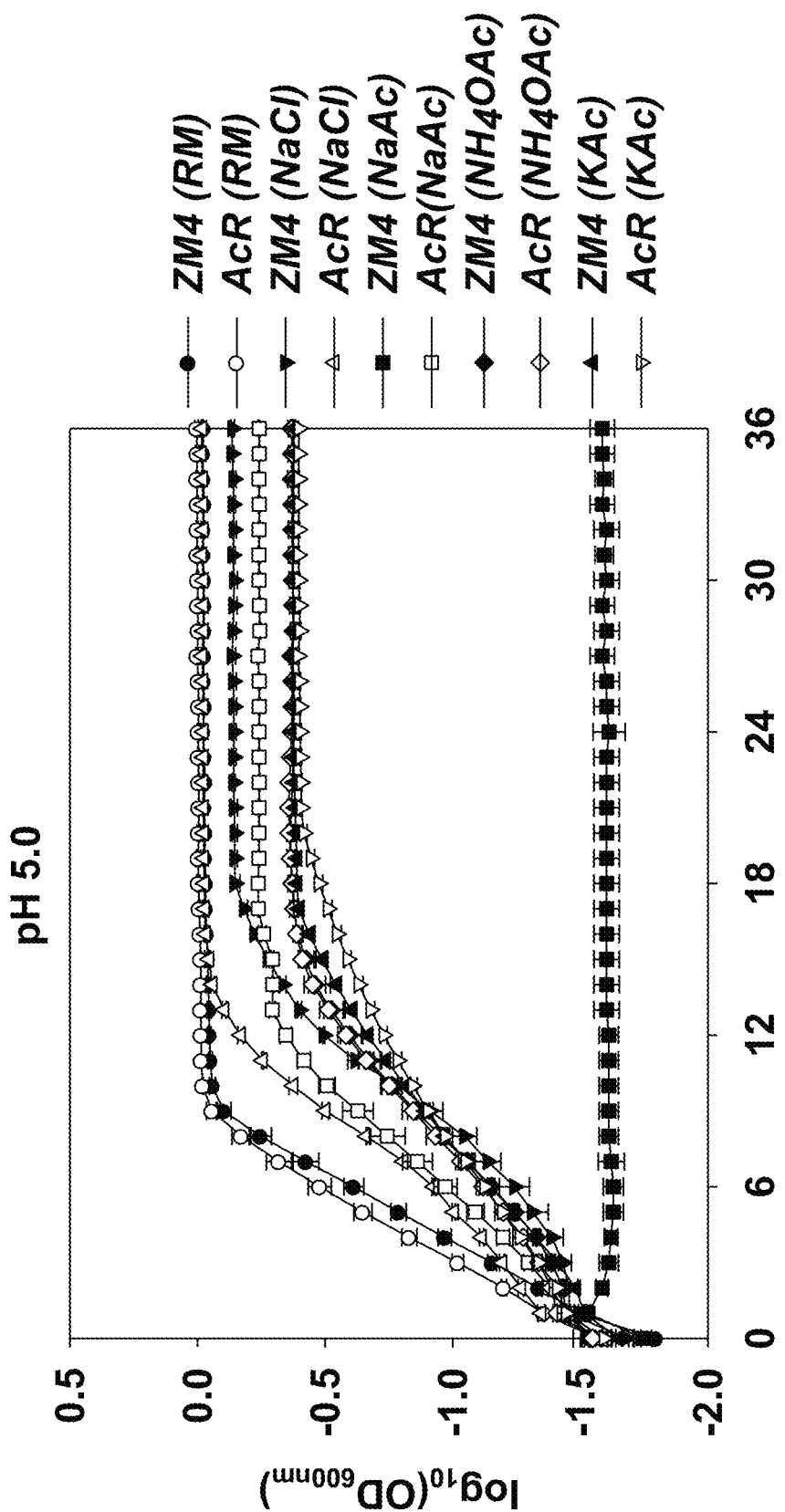
Figure 8A:
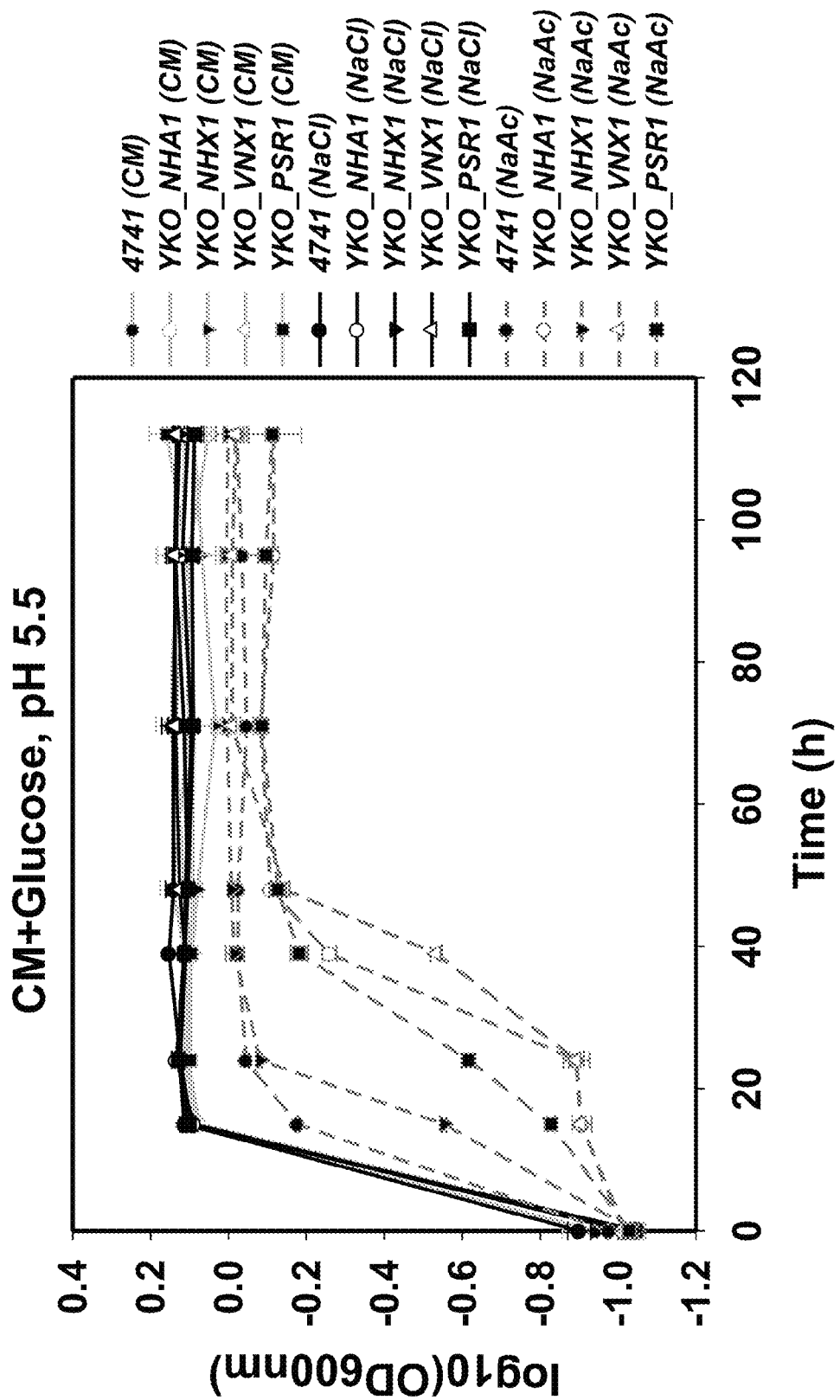
FIGS. 8A-8D demonstrate that sodium proton antiporter proteins in *S. cerevisiae* are responsible for sodium acetate tolerance.
Figure 8B:
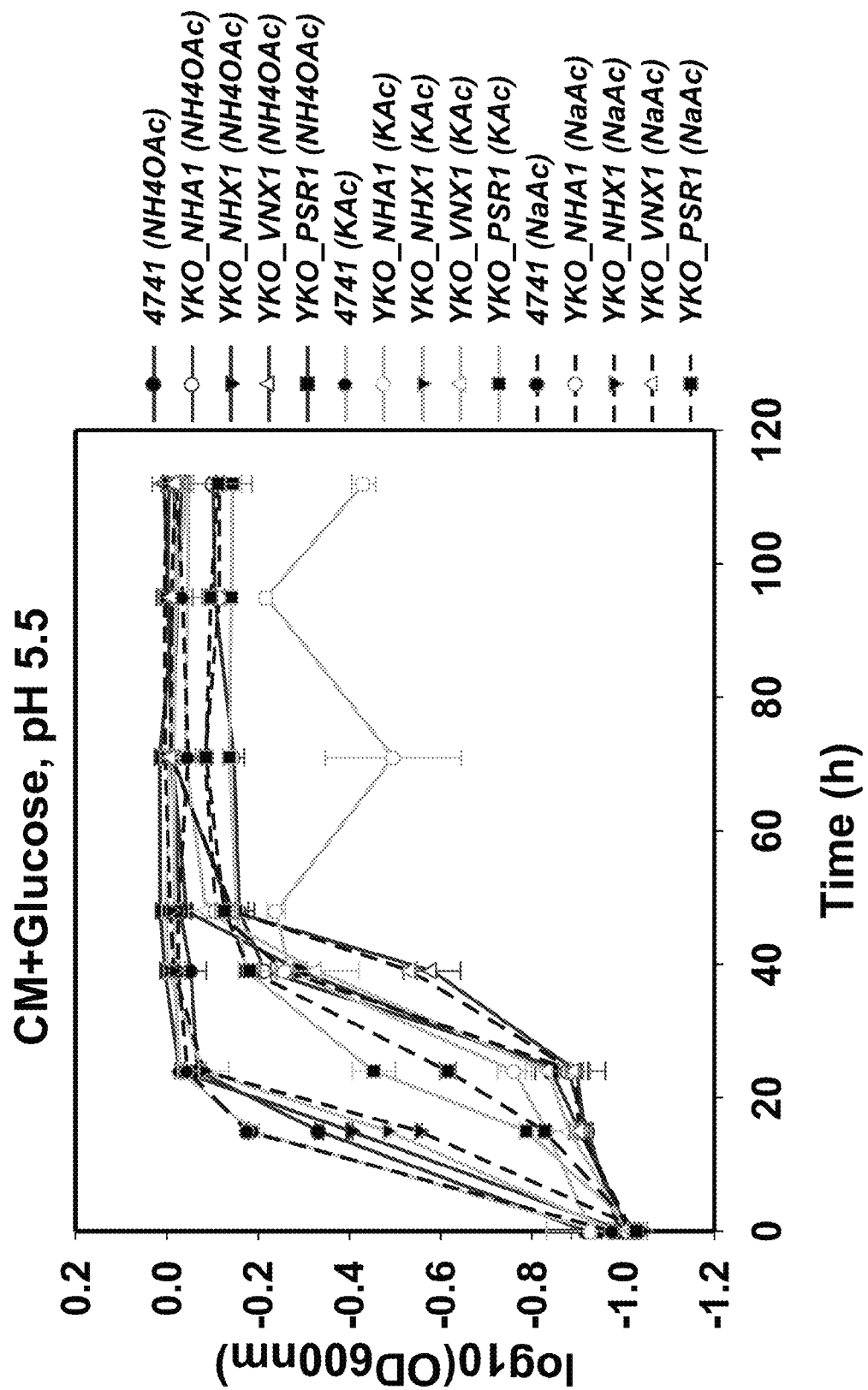
Figure 8C:
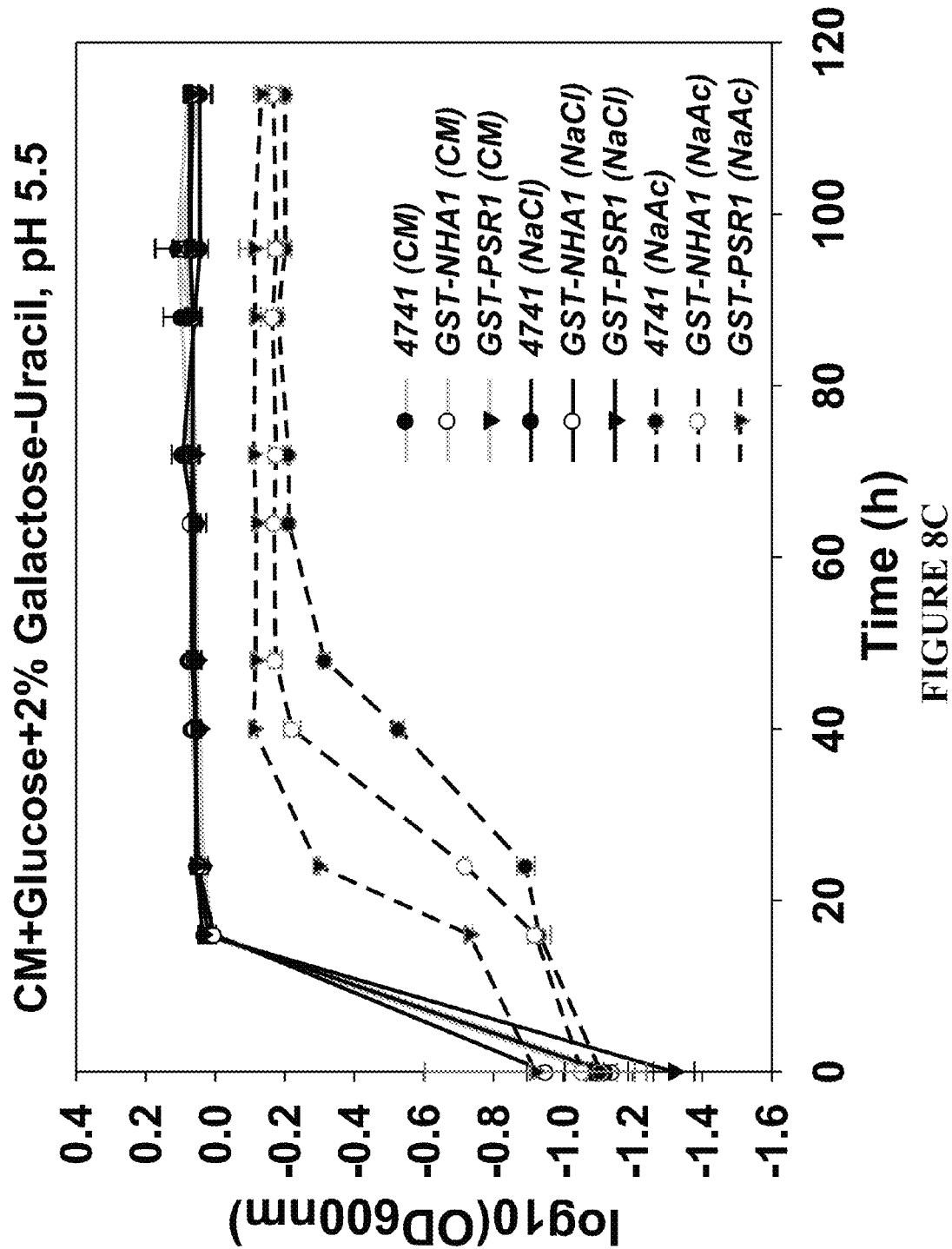
Figure 8D:
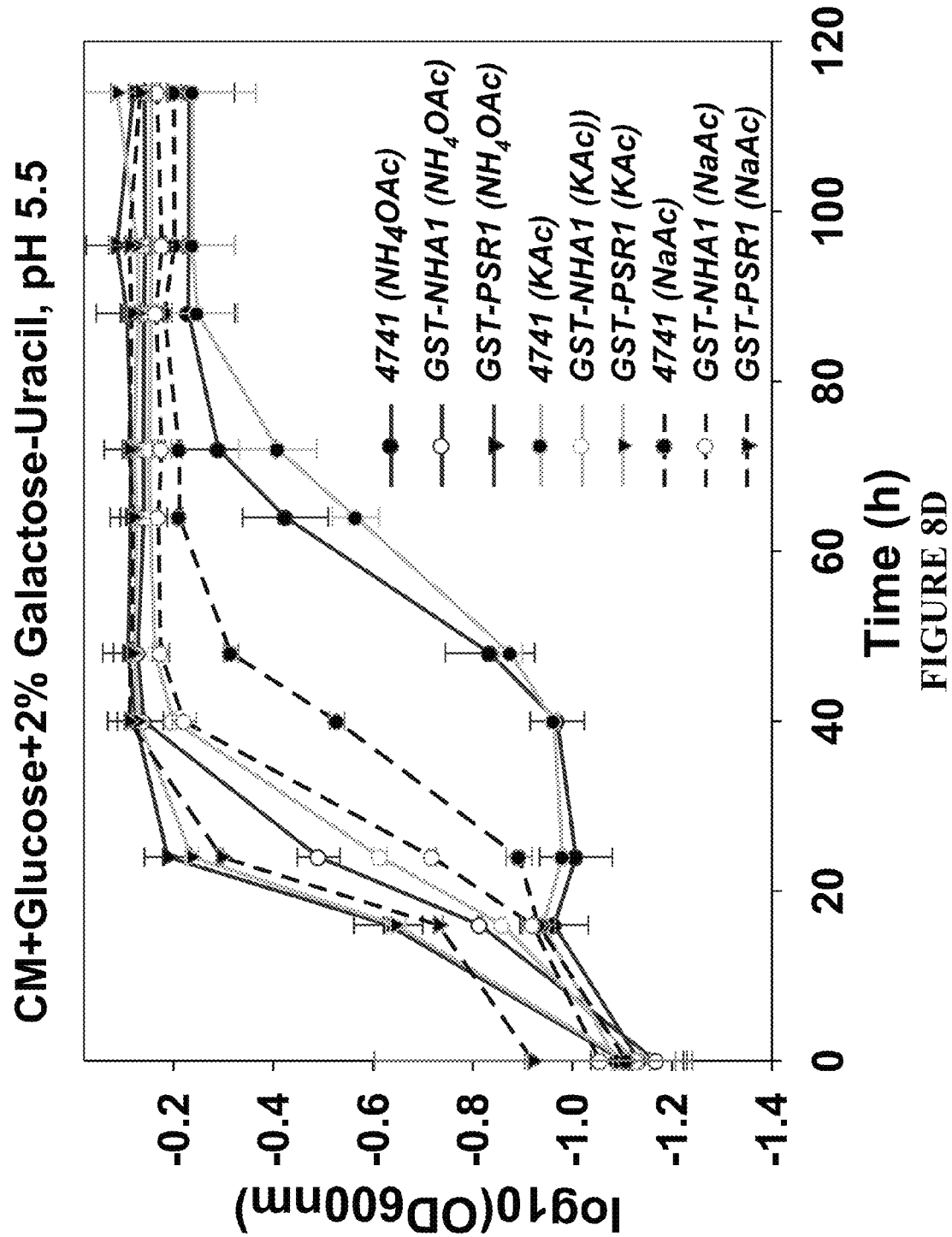

ZM4 and AcR strains were grown in the presence of the same molar concentrations (195 mM) of sodium chloride (NaCl), sodium acetate (NaAc), potassium acetate (KAc), or ammonium acetate ($NH_4OAc$). Both the sodium and acetate ions had a toxic effect on Z. mobilis growth, with decreases in both growth rate and final cell density (Table 3; FIG. 7). The acetate ion was more toxic than the sodium ion: Z. mobilis grew more rapidly in the presence of 195 mM NaCl and the final cell density was higher compared to growth in the presence of same molar concentration of $NH_4OAc$ or KAc (Table 3). NaAc was more inhibitory than the same molar concentration (195 mM) of KAc or $NH_4OAc$ for ZM4 and the combination of elevated Na+ and Ac− ions appeared to exert a synergistic inhibitory effect for strain ZM4 with the growth of Z. mobilis totally inhibited (Table 3; FIG. 7). The AcR strain was selected for sodium acetate tolerance, but also had enhanced tolerance to NaCl, but not $NH_4OAc$ or KAc compared to the Z. mobilis wild-type ZM4 (Table 3; FIG. 7). Strain ZM4DM0117 and ZM4 harboring the nhaA-expressing plasmid p42-0119 similarly had enhanced NaCl tolerance that did not extend to $NH_4OAc$ or KAc (Table 3; FIG. 7). The increased tolerance to NaAc for these strains may therefore be due mostly to an increased sodium ion tolerance arising from the overexpression of Na+/H+ antiporter gene nhaA.

TABLE 3

Growth rate and final cell density of different Z. mobilis strains in the presence of NaCl, $NH_4OAc$, or KAc.

| | | ZM4 | AcR | ZM4DM0117 | ZM4IM0117 | ZM4(p42-0119) |
|---|---|---|---|---|---|---|
| Growth rate (hour$^{-1}$) | RM | 0.42 ± 0.01 | 0.39 ± 0.01 | 0.39 ± 0.009 | 0.40 ± 0.00 | 0.39 ± 0.004 |
| | RM (NaCl, 195 mM) | 0.24 ± 0.008 | 0.29 ± 0.005 | 0.31 ± 0.006 | 0.19 ± 0.01 | 0.26 ± 0.01 |
| | RM ($NH_4OAc$, 195 mM) | 0.20 ± 0.008 | 0.19 ± 0.005 | 0.21 ± 0.001 | 0.21 ± 0.002 | 0.18 ± 0.001 |
| | RM (KAc, 195 mM) | 0.15 ± 0.004 | 0.12 ± 0.000 | 0.17 ± 0.000 | 0.17 ± 0.005 | 0.12 ± 0.001 |
| | RM (NaAc, 195 mM) | NA | 0.29 ± 0.04 | 0.15 ± 0.003 | NA | 0.22 ± 0.006 |
| | RM (NaAc, 146 mM) | 0.25 ± 0.002 | 0.32 ± 0.01 | 0.33 ± 0.002 | 0.28 ± 0.008 | 0.29 ± 0.01 |
| Final Cell Density ($OD_{600nm}$) | RM | 0.95 ± 0.006 | 1.01 ± 0.006 | 0.91 ± 0.001 | 0.92 ± 0.02 | 0.99 ± 0.001 |
| | RM (NaCl, 195 mM) | 0.73 ± 0.01 | 0.96 ± 0.01 | 0.88 ± 0.002 | 0.70 ± 0.02 | 0.89 ± 0.01 |
| | RM ($NH_4OAc$, 195 mM) | 0.43 ± 0.01 | 0.42 ± 0.006 | 0.41 ± 0.002 | 0.42 ± 0.005 | 0.36 ± 0.03 |
| | RM (KAc, 195 mM) | 0.42 ± 0.002 | 0.40 ± 0.000 | 0.41 ± 0.01 | 0.40 ± 0.01 | 0.34 ± 0.001 |
| | RM (NaAc, 195 mM) | NA | 0.63 ± 0.02 | 0.48 ± 0.007 | NA | 0.55 ± 0.006 |
| | RM (NaAc, 146 mM) | 0.55 ± 0.01 | 0.72 ± 0.008 | 0.64 ± 0.005 | 0.59 ± 0.006 | 0.68 ± 0.005 |

"NA" indicates that the data are not available due to the lack of growth in that condition. The concentration for all the chemicals supplemented into the RM is the number after the chemical.

NaCl: sodium chloride, $NH_4OAc$: ammonium acetate,

KAc: potassium acetate,

NaAc: sodium acetate.

This experiment has been repeated at least three times with similar result. Duplicates biological replicates were used for each condition.

Example 5

This example describes experiments conducted to examine the function of sodium/proton antiporters in yeast *S. cerevisiae*.

Yeast has three sodium/proton antiporters. NHA1 (YLR138W) is a Na+/H+ antiporter involved in sodium and potassium efflux through the plasma membrane; required for alkali cation tolerance at acidic pH. VNX1 (YNL321W) is vacuolar Na+/H+ exchanger. NHX1 (YDR456W) is an endosomal Na+/H+ exchanger, required for intracellular sequestration of Na+, and required for osmotolerance to acute hypertonic shock.

*S. cerevisiae* deletion mutants of the above three Na+/H+ exchangers and an NHA1-overexpression strain were obtained from Open Biosystems company (Table 1). The growth curves of the mutants, NHA1-overexpression strain and the wild-type strain cultured in a rich YPD media and minimum complete medium (CM) containing NaAc, NH$_4$OAc, or KAc were tested using the Bioscreen system. Specifically, *S. cerevisiae* strains were grown in CM with 2% glucose for wild-type BY4741 and the deletion mutants, CM with 2% glucose minus uracil for GST over-expression strains with 2% galactose added for gene induction. A 5-μL culture was then transferred into 300-μL CM broth in the Bioscreen plate. The growth differences among different strains were monitored by Bioscreen (Growth Curve USA, NJ). Strains included in this experiment are listed in Table 1. This experiment has been repeated at least three times with similar result.

As shown in FIGS. 8A-8D, each Na+/H+ antiporter mutant was more sensitive to acetate than the wild-type control strain, and tolerance to each of NaAc, NH$_4$OAc, and KAc could be enhanced by expression of plasmid encoded yeast Na+/H+ antiporter genes. These data indicate that Na+/H+ antiporter genes in *S. cerevisiae* are involved in acetate tolerance, and are consistent with earlier reports that these yeast systems can function as monovalent cation/H+ antiporters (Banuelos et al. 1998; Cagnac et al. 2007).

REFERENCES

1. Alexeyev, M. F. (1999). "The pKNOCK series of broad-host-range mobilizable suicide vectors for gene knockout and targeted DNA insertion into the chromosome of gram-negative bacteria." *Biotechnigues* 26: 824-826.
2. Almeida, J. R. M., T. Modig, et al. (2007). "Increased tolerance and conversion of inhibitors in lignocellulosic hydrolysates by *Saccharomyces cerevisiae*." *Journal of Chemical Technology and Biotechnology* 82(4): 340-349.
3. Arkin I T, et al. (2007) Mechanism of Na+/H+ antiporting. *Science* 317:799-803
4. Banuelos M A, Sychrova H, Bleykasten-Grosshans C, Souciet J L, Potier S (1998) The Nha1
5. antiporter of *Saccharomyces cerevisiae* mediates sodium and potassium efflux. Microbiology 144:2749-2758. Cagnac O, Leterrier M, Yeager M, Blumwald E (2007) Identification and characterization of Vnx1p, a novel type of vacuolar monovalent cation/H+ antiporter of *Saccharomyces cerevisiae*. J Biol Chem 282:24284-24293.
6. Baumler, D. J., K. F. Hung, et al. (2006). "Enhancement of acid tolerance in *Zymomonas mobilis* by a proton-buffering peptide." *Appl. Biochem. Biotechnol.* 134(1): 15-26.
7. Chinnawirotpisan, P., G. Theeragool, et al. (2003). "Quinoprotein alcohol dehydrogenase is involved in catabolic acetate production, while NAD-dependent alcohol dehydrogenase in ethanol assimilation in *Acetobacter pasteurianus* SKU1108." *J. Biosci. Bioeng.* 96(6): 564-571.
8. Deanda, K., M. Zhang, et al. (1996). "Development of an arabinose-fermenting *Zymomonas mobilis* strain by metabolic pathway engineering." *Appl. Environ. Microbiol.* 62(12): 4465-4470.
9. Denef, V. J., J. A. Klappenbach, et al. (2006). "Genetic and genomic insights into the role of benzoate catabolic pathway redundancy in *Burkholderia xenovorans* LB400." *Appl. Environ. Microbiol.* 72(1): 585-595.
10. Dien, B. S., M. A. Cotta, et al. (2003). "Bacteria engineered for fuel ethanol production: current status." *Appl. Microbiol. Biotechnol.* 63(3): 258-266.
11. Fukaya, M., H. Takemura, et al. (1990). "Cloning of genes responsible for acetic acid resistance in *Acetobacter aceti*." *J. Bacteriol.* 172(4): 2096-2104.
12. Fukaya, M., H. Takemura, et al. (1993). "The aarC gene responsible for acetic acid assimilation confers acetic acid resistance on *Acetobacter aceti*." *J. Ferment. Bioenq.* 76(4): 270-275.
13. Gao, X., Z. Ren, et al. (2003). "Overexpression of SOD2 increases salt tolerance of *Arabidopsis*." *Plant Physiol* 133 (4): 1873-81.
14. Gunasekaran, P. and K. C. Raj (1999). "Ethanol fermentation technology—*Zymomonas mobilis*." *Current Science* 77(1): 56-68.
15. Hahnenberger, K. M., Z. P. Jia, et al. (1996). "Functional expression of the *Schizosaccharomyces pombe* Na+/H+ antiporter gene, sod2, in *Saccharomyces cerevisiae*." *Proceedings of the National Academy of Sciences of the United States of America* 93(10): 5031-5036.
16. Jeon, Y. J., C. J. Svenson, et al. (2002). "Kinetic analysis of ethanol production by an acetate-resistant strain of recombinant *Zymomonas mobilis*." *Biotechnol. Lett.* 24(10): 819-824.
17. Jia, Z. P., N. Mccullough, et al. (1992). "Gene Amplification at a Locus Encoding a Putative Na+/H+ Antiporter Confers Sodium and Lithium Tolerance in Fission Yeast." *Embo Journal* 11 (4): 1631-1640.
18. Joachimstahl, E., K. D. Haggett, et al. (1998). "A mutant of *Zymomonas* mobilis ZM4 capable of ethanol production from glucose in the presence of high acetate concentrations." *Biotechnol. Lett.* 20(2): 137-142.
19. Joachimsthal, E. L. and P. L. Rogers (2000). "Characterization of a high-productivity recombinant strain of *Zymomonas mobilis* for ethanol production from glucose/xylose mixtures." *Appl. Biochem. Biotechnol.* 84-6: 343-356.
20. Kadar, Z., S. F. Maltha, et al. (2007). "Ethanol fermentation of various pretreated and hydrolyzed substrates at low initial pH." *Appl. Biochem. Biotechnol.* 137: 847-858.
21. Kim, I. S., K. D. Barrow, et al. (2000). "Nuclear magnetic resonance studies of acetic acid inhibition of rec *Zymomonas mobilis* ZM4(pZB5)." *Appl. Biochem. Biotechnol.* 84-6: 357-370.
22. Lawford, H. G. and J. D. Rousseau (1993). "The effect of acetic acid on fuel ethanol-Production by *Zymomonas*." *Appl. Biochem. Biotechnol.* 39: 687-699.
23. Lawford, H. G. and J. D. Rousseau (1993). "Effects of pH and acetic acid on glucose and xylose metabolism by a genetically engineered ethanologenic *Escherichia coli*." Appl. Biochem. Biotechnol. 39: 301-322.
24. Lawford, H. G. and J. D. Rousseau (1998). "Improving fermentation performance of recombinant *Zymomonas* in acetic acid-containing media." *Appl. Biochem. Biotechnol.* 70-2: 161-172.

25. Lawford, H. G. and J. D. Rousseau (2001). "Fermentation performance assessment of a genomically integrated xylose-utilizing recombinant of *Zymomonas mobilis* 39676." *Appl. Biochem. Biotechnol.* 91-3: 117-131.
26. Lawford, H. G. and J. D. Rousseau (2003). "Cellulosic fuel ethanol—Alternative fermentation process designs with wild-type and recombinant *Zymomonas mobilis*." *Appl. Biochem. Biotechnol.* 105: 457-469.
27. Lawford, H. G., J. D. Rousseau, et al. (1999). "Fermentation performance characteristics of a prehydrolyzate-adapted xylose-fermenting recombinant *Zymomonas* in batch and continuous fermentations." *Appl. Biochem. Biotechnol.* 77-9: 191-204.
28. Lawford, H. G., J. D. Rousseau, et al. (2001). "Comparative ethanol productivities of different *Zymomonas* recombinants fermenting oat hull hydrolysate." *Appl. Biochem. Biotechnol.* 91-3: 133-146.
29. Liu, Z. L., P. J. Slininger, et al. (2005). "Enhanced biotransformation of furfural and hydroxymethylfurfural by newly developed ethanologenic yeast strains." *Appl. Biochem. Biotechnol.* 121: 451-460.
30. Matsushita, K., T. Inoue, et al. (2005). "*Acetobacter aceti* possesses a proton motive force-dependent efflux system for acetic acid." *J. Bacteriol.* 187 (13): 4346-4352.
31. McMillan, J. D. (1994). Conversion of hemicellulose hydrolyzates to ethanol. *Enzymatic Conversion of Biomass for Fuels Production*. M. E. B. J. O. O. R. P. Himmel. 566: 411-437.
32. Mohagheghi, A., N. Dowe, et al. (2004). "Performance of a newly developed integrant of *Zymomonas mobilis* for ethanol production on corn stover hydrolysate." *Biotechnol. Lett.* 26 (4): 321-325.
33. Mohagheghi, A., K. Evans, et al. (2002). "Cofermentation of glucose, xylose, and arabinose by genomic DNA-integrated xylose/arabinose fermenting strain of *Zymomonas mobilis AX*101." *Appl. Biochem. Biotechnol.* 98-100: 885-898.
34. Mullins, E. A., J. A. Francois, et al. (2008). "A specialized citric acid cycle requiring succinyl-coenzyme A (CoA): Acetate CoA-transferase (AarC) confers acetic acid resistance on the acidophile *Acetobacter aceti*." *J. Bacteriol.* 190 (14): 4933-4940.
35. Okumura, H., T. Uozumi, et al. (1985). "Biochemical characteristics of spontaneous mutants of *Acetobacter aceti* deficient in ethanol oxidation." *Agri. Biological Chem.* 49(8): 2485-2487.
36. Panesar, P. S., S. S. Marwaha, et al. (2006). "*Zymomonas mobilis*: an alternative ethanol producer." *J. Chem. Technol. Biotechnol.* 81 (4): 623-635.
37. Pelletier et al. ("A general system for studying protein-protein interactions in gram-negative bacteria", *Journal of Proteome Research* 2008, 7(8):3319-3328).
38. Prior, C., S. Potier, et al. (1996). "Characterization of the NHA1 gene encoding a Na+/H+-antiporter of the yeast *Saccharomyces cerevisiae*." *Febs Letters* 387(1): 89-93.
39. Ranatunga, T. D., J. Jervis, et al. (1997). "Identification of inhibitory components toxic toward *Zymomonas mobilis* CP4(pZB5) xylose fermentation." *Appl. Biochem. Biotechnol.* 67 (3): 185-198.
40. Reisch, M. (2006). "Fuels of the future chemistry and agriculture join to make a new generation of renewable fuels." *Chem. Eng. News* 84: 3.
41. Rogers, P. L., A. E. Goodman, et al. (1984). "*Zymomonas* ethanol fermentations." *Microbiol. Sci.* 1 (6): 133-136.
42. Rogers, P. L., Y. J. Jeon, et al. (2007). *Zymomonas mobilis* for fuel ethanol and higher value products. *Biofuels.* 108: 263-288.
43. Steiner, P. and U. Sauer (2003). "Overexpression of the ATP-dependent helicase RecG improves resistance to weak organic acids in *Escherichia coli*." *Applied Microbiology and Biotechnology* 63(3): 293-299.
44. Swings, J. and J. De Ley (1977). "The biology of *Zymomonas mobilis*." *Bacteriol. Rev.* 41: 1-46.
45. Takahashi, C. M., D. F. Takahashi, et al. (1999). "Effects of acetate on the growth and fermentation performance of *Escherichia coli* KO11." *Appl. Biochem. Biotechnol.* 81 (3): 193-203.
46. Takemura, H., S. Horinouchi, et al. (1991). "Novel insertion sequence IS1380 from *Acetobacter pasteurianus* is involved in loss of ethanol oxidizing ability." *J. Bacteriol.* 173(22): 7070-7076.
47. Wu, L. Q., Z. M. Fan, et al. (2005). "Over-expression of the bacterial nhaA gene in rice enhances salt and drought tolerance." *Plant Science* 168(2): 297-302.
48. Yang, S., Tschaplinski, T. J., et al. (2009). "Transcriptomic and metabolomic profiling of *Zymomonas* mobilis during aerobic and anaerobic fermentations." *BMC Genomics* 10: 34.
49. Zhang, M., C. Eddy, et al. (1995). "Metabolic engineering of a pentose metabolism pathway in ethanologenic *Zymomonas mobilis*." *Science* 267(5195): 240-243.
50. U.S. Pat. No. 5,712,133
51. U.S. Pat. No. 5,726,053
52. U.S. Pat. No. 5,843,760
53. U.S. Pat. No. 5,514,583
54. U.S. Pat. No. 7,285,403

What is claimed is:

1. A method of producing ethanol from a cellulosic biomass material, comprising:
   (a) providing a microorganism genetically modified to contain an expression vector coding for a sodium-proton antiporter, wherein the genetic modification results in increased expression of a sodium-proton antiporter in said microorganism and elevated resistance to acetate as compared to an unmodified strain of said microorganism;
   (b) adding the genetically modified microorganism of (a) to a fermentation mixture comprising a cellulosic biomass material and/or fermentation substrates derived from said cellulosic biomass material;
   (c) allowing said microorganism to ferment and produce ethanol; and
   (d) recovering ethanol produced.

2. The method of claim 1, wherein said microorganism is selected from bacteria or fungi.

3. The method of claim 2, wherein said microorganism is a bacterial species selected from *Acetobacterium, Bacillus, Streptococcus, Clostridium, Zymomonas* sp., and *Gluconobacter* sp.

4. The method of claim 2, wherein said microorganism is a fungal species selected from *Saccharomyces* sp., *Kluyveromyces* sp., *Pichia* sp., *Candida* sp., and *Schizosaccharomycetes* sp.

5. The method of claim 1, wherein said sodium-proton antiporter is selected from the group consisting of a plasma membrane sodium-proton antiporter, an endosomal sodium-proton antiporter, and a vacuolar sodium-proton antiporter.

6. The method of claim 5, wherein said sodium-proton antiporter is a plasma membrane sodium-proton antiporter native to said microorganism.

7. The method of claim 1, wherein said microorganism is *Z. mobilis*.

8. The method of claim 7, wherein said sodium-proton antiporter comprises the protein sequence as set forth in SEQ ID NO: 2.

9. The method of claim 1, wherein said microorganism is *S. cerevisiae*.

10. The method of claim 9, wherein said sodium-proton antiporter is the plasma membrane sodium-proton antiporter comprising the amino acid sequence of SEQ ID NO: 15.

11. The method of claim 1, wherein the expression vector is an integrative vector.

12. The method of claim 1, wherein the expression vector is a replicative vector.

* * * * *

SEQUENCE LISTING

```
<160> NUMBER OF SEQ ID NOS: 15

<210> SEQ ID NO 1
<211> LENGTH: 1167
<212> TYPE: DNA
<213> ORGANISM: Zymomonas mobilis

<400> SEQUENCE: 1
atgcggtttt ctattcgtcg attttttca gctgcctctg gcggcgcgat tatcctgctc      60
ttatccgccc ttcttggatt gcttttatcc aactcttttt tgtccgaaag ttattttaag    120
gtgcttcatc tgaaaatgcc attttcggct ttggatgatg ccctaatct ggcagagttt     180 atttctattg cgccgatgtc gcttttcttt tttgtcgtta ttgcagaaat aaaagaagaa    240
```

```
attatttcgg gacatctggc ttctttccgg cgggttatct tgcccctgat ttcagcttta        300
gggggaatga tgattcccgc ttgtctatat gggctgatta catctggtca tttagaagta        360
agccgtggct gggcgatacc aatcgcaacg gatgccgcct ttaccttacc tattattttg        420
gcgttaggac gccatgtttc tgaaggcgca agggtctggt taatggcttt ggctattttc        480
gatgacctat taggtattgt tgttattgct cttttttatg cgtcccattt gaatggatat        540
gccctttttcg cagcgggctt aatcactgcc gtgatgattg gctgaataa aaaatctgtc        600
cagaatttat gggtctatgc ttctgctggt gttgtcttat ggtgggctct attggttttct        660
ggcctccatc ctaccatcgc cggtgtgata acaggtcttg cccttccttc tgttgcggat        720
caaccggaaa aagcctctcc tttagagcga ggaaaacaaa ttattgcgcc tgggtgaca        780
tggctcattc tgcctttatt tggctttgtt agtatgggaa tgtcgctgtc tgctatgtcc        840
tttcatgttt tgctggcacc tgtccctttg ggggttgcgt tgggcttgtt tttgggaaag        900
cccatagggg ttttttggtgc tactataatg gcaacccgac taaagattgc gacccttcct        960
aagggaactt ccttgaggat gttgttcggg ctatccttgt tatgcggtat cggttttacg       1020
attagtttat ttattgcaga attggctttt tctggttcag attttctggt tccggccaaa       1080
tatgggatat tgatgggctc tctcttatcc gctttagctg gatggttatg gttacgtttt       1140
ttaaagtttc cggcaaaagg cgtttga                                           1167
```

```
<210> SEQ ID NO 2
<211> LENGTH: 388
<212> TYPE: PRT
<213> ORGANISM: Zymomonas mobilis

<400> SEQUENCE: 2

Met Arg Phe Ser Ile Arg Arg Phe Phe Ser Ala Ala Ser Gly Gly Ala
1               5                   10                  15

Ile Ile Leu Leu Leu Ser Ala Leu Leu Gly Leu Leu Leu Ser Asn Ser
            20                  25                  30

Phe Leu Ser Glu Ser Tyr Phe Lys Val Leu His Leu Lys Met Pro Phe
        35                  40                  45

Ser Ala Leu Asp Asp Ala Pro Asn Leu Ala Glu Phe Ile Ser Ile Ala
    50                  55                  60

Pro Met Ser Leu Phe Phe Phe Val Val Ile Ala Glu Ile Lys Glu Glu
65                  70                  75                  80

Ile Ile Ser Gly His Leu Ala Ser Phe Arg Arg Val Ile Leu Pro Leu
                85                  90                  95

Ile Ser Ala Leu Gly Gly Met Met Ile Pro Ala Cys Leu Tyr Gly Leu
            100                 105                 110

Ile Thr Ser Gly His Leu Glu Val Ser Arg Gly Trp Ala Ile Pro Ile
        115                 120                 125

Ala Thr Asp Ala Ala Phe Thr Leu Pro Ile Ile Leu Ala Leu Gly Arg
    130                 135                 140

His Val Ser Glu Gly Ala Arg Val Trp Leu Met Ala Leu Ala Ile Phe
145                 150                 155                 160

Asp Asp Leu Leu Gly Ile Val Val Ile Ala Leu Phe Tyr Ala Ser His
                165                 170                 175

Leu Asn Gly Tyr Ala Leu Phe Ala Ala Gly Leu Ile Thr Ala Val Met
            180                 185                 190

Ile Gly Leu Asn Lys Lys Ser Val Gln Asn Leu Trp Val Tyr Ala Ser
        195                 200                 205
```

-continued

```
Ala Gly Val Val Leu Trp Trp Ala Leu Leu Val Ser Gly Leu His Pro
    210                 215                 220

Thr Ile Ala Gly Val Ile Thr Gly Leu Ala Leu Pro Ser Val Ala Asp
225                 230                 235                 240

Gln Pro Glu Lys Ala Ser Pro Leu Glu Arg Gly Lys Gln Ile Ile Ala
                245                 250                 255

Pro Trp Val Thr Trp Leu Ile Leu Pro Leu Phe Gly Phe Val Ser Met
                260                 265                 270

Gly Met Ser Leu Ser Ala Met Ser Phe His Val Leu Leu Ala Pro Val
                275                 280                 285

Pro Leu Gly Val Ala Leu Gly Leu Phe Leu Gly Lys Pro Ile Gly Val
                290                 295                 300

Phe Gly Ala Thr Ile Met Ala Thr Arg Leu Lys Ile Ala Thr Leu Pro
305                 310                 315                 320

Lys Gly Thr Ser Leu Arg Met Leu Phe Gly Leu Ser Leu Leu Cys Gly
                325                 330                 335

Ile Gly Phe Thr Ile Ser Leu Phe Ile Ala Glu Leu Ala Phe Ser Gly
                340                 345                 350

Ser Asp Phe Leu Val Pro Ala Lys Tyr Gly Ile Leu Met Gly Ser Leu
                355                 360                 365

Leu Ser Ala Leu Ala Gly Trp Leu Trp Leu Arg Phe Leu Lys Phe Pro
370                 375                 380

Ala Lys Gly Val
385

<210> SEQ ID NO 3
<211> LENGTH: 158
<212> TYPE: DNA
<213> ORGANISM: Zymomonas mobilis

<400> SEQUENCE: 3
tagagtcaaa gagtttaatt tattttacgg ggaagggggg ctttggctcc ccttttctgt      60
attcatgaaa gaggcggttt ttatatcaaa aaagagggcg atattagaca atagcttggt     120
ttgattttta gctatacgtt tgatcaataa ggcaggat                             158

<210> SEQ ID NO 4
<211> LENGTH: 98
<212> TYPE: DNA
<213> ORGANISM: Zymomonas mobilis

<400> SEQUENCE: 4
tagagtcaaa gagtttaatt tattttacgg ggaagggggg ctttggctcc ccttttctgt      60
attcatgaaa gaggcggttt ttatatcaaa aaagaggg                              98

<210> SEQ ID NO 5
<211> LENGTH: 60
<212> TYPE: DNA
<213> ORGANISM: Zymomonas mobilis

<400> SEQUENCE: 5
cgatattaga caatagcttg gtttgatttt tagctatacg tttgatcaat aaggcaggat      60

<210> SEQ ID NO 6
<211> LENGTH: 20
<212> TYPE: DNA
<213> ORGANISM: Artificial Sequence
<220> FEATURE:
```

<223> OTHER INFORMATION: Synthetic oligonucleotide primer

<400> SEQUENCE: 6
gtatcgacgt caccggtctt    20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 7
ggctccatca gacagttggt    20

<210> SEQ ID NO 8
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 8
cgagctcttt cgtcgataag gaatcagc    28

<210> SEQ ID NO 9
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 9
gccgcggcgg aagtcaacca gatgata    27

<210> SEQ ID NO 10
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 10
gcatatgcga tattagacaa tagcttg    27

<210> SEQ ID NO 11
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 11
cgaattctat cgcagcaaaa gccataa    27

<210> SEQ ID NO 12
<211> LENGTH: 1167
<212> TYPE: DNA
<213> ORGANISM: Escherichia coli

<400> SEQUENCE: 12
gtgaaacatc tgcatcgatt ctttagcagt gatgcctcgg gaggcattat tcttatcatt    60
gccgctatcc tggcgatgat tatggccaac agcggcgcaa ccagtggatg gtatcacgac    120
tttctggaga cgccggttca gctccgggtt ggttcactcg aaatcaacaa aaacatgctg    180

```
ttatggataa atgacgcgct gatggcggta ttttcctgt tagtcggtct ggaagttaaa      240
cgtgaactga tgcaaggatc gctagccagc ttacgccagg ccgcatttcc agttatcgcc      300
gctattggtg ggatgattgt gccggcatta ctctatctgg cttttaacta tgccgatccg      360
attaccgcg aagggtgggc gatcccggcg gctactgaca ttgcttttgc acttggtgta       420
ctggcgctgt gggaagtcg tgttccgtta gcgctgaaga tctttttgat ggctctggct      480
attatcgacg atcttggggc catcattatc atcgcattgt tctacactaa tgacttatcg      540
atggcctctc ttggcgtcgc ggctgtagca attgcggtac tcgcggtatt gaatctgtgt      600
ggtgcacgcc gcacgggcgt ctatattctt gttggcgtgg tgttgtggac tgcggtgttg      660
aaatcggggg ttcacgcaac tctggcgggg gtaattgtcg gcttctttat cctttgaaa      720
gagaagcatg ggcgttctcc agcgaagcga ctggagcatg tgttgcaccc gtgggtggcg     780
tatctgattt tgccgctgtt tgcatttgct aatgctggcg tttcactgca aggcgtcacg      840
ctggatggct tgacctccat tctgccattg gggatcatcg ctggcttgct gattggcaaa      900
ccgctgggga ttagtctgtt ctgctggttg gcgctgcgtt tgaaactggc gcatctgcct      960
gagggaacga cttatcagca aattatggtg gtggggatcc tgtgcggtat cggtttact     1020
atgtctatct ttattgccag cctggccttt ggtagcgtag atccagaact gattaactgg    1080
gcgaaactcg gtatcctggt cggttctatc tcttcggcgg taattggata cagctggtta    1140
cgcgttcgtt tgcgtccatc agtttga                                         1167

<210> SEQ ID NO 13
<211> LENGTH: 388
<212> TYPE: PRT
<213> ORGANISM: Escherichia coli

<400> SEQUENCE: 13

Met Lys His Leu His Arg Phe Phe Ser Ser Asp Ala Ser Gly Gly Ile
1               5                   10                  15

Ile Leu Ile Ile Ala Ala Ile Leu Ala Met Ile Met Ala Asn Ser Gly
            20                  25                  30

Ala Thr Ser Gly Trp Tyr His Asp Phe Leu Glu Thr Pro Val Gln Leu
        35                  40                  45

Arg Val Gly Ser Leu Glu Ile Asn Lys Asn Met Leu Leu Trp Ile Asn
    50                  55                  60

Asp Ala Leu Met Ala Val Phe Phe Leu Leu Val Gly Leu Glu Val Lys
65                  70                  75                  80

Arg Glu Leu Met Gln Gly Ser Leu Ala Ser Leu Arg Gln Ala Ala Phe
                85                  90                  95

Pro Val Ile Ala Ala Ile Gly Gly Met Ile Val Pro Ala Leu Leu Tyr
            100                 105                 110

Leu Ala Phe Asn Tyr Ala Asp Pro Ile Thr Arg Glu Gly Trp Ala Ile
        115                 120                 125

Pro Ala Ala Thr Asp Ile Ala Phe Ala Leu Gly Val Leu Ala Leu Leu
    130                 135                 140

Gly Ser Arg Val Pro Leu Ala Leu Lys Ile Phe Leu Met Ala Leu Ala
145                 150                 155                 160

Ile Ile Asp Asp Leu Gly Ala Ile Ile Ile Ala Leu Phe Tyr Thr
                165                 170                 175

Asn Asp Leu Ser Met Ala Ser Leu Gly Val Ala Val Ala Ile Ala
            180                 185                 190
```

```
Val Leu Ala Val Leu Asn Leu Cys Gly Ala Arg Arg Thr Gly Val Tyr
            195                 200                 205
Ile Leu Val Gly Val Val Leu Trp Thr Ala Val Leu Lys Ser Gly Val
        210                 215                 220
His Ala Thr Leu Ala Gly Val Ile Val Gly Phe Phe Ile Pro Leu Lys
225                 230                 235                 240
Glu Lys His Gly Arg Ser Pro Ala Lys Arg Leu Glu His Val Leu His
                245                 250                 255
Pro Trp Val Ala Tyr Leu Ile Leu Pro Leu Phe Ala Phe Ala Asn Ala
            260                 265                 270
Gly Val Ser Leu Gln Gly Val Thr Leu Asp Gly Leu Thr Ser Ile Leu
        275                 280                 285
Pro Leu Gly Ile Ile Ala Gly Leu Leu Ile Gly Lys Pro Leu Gly Ile
    290                 295                 300
Ser Leu Phe Cys Trp Leu Ala Leu Arg Leu Lys Leu Ala His Leu Pro
305                 310                 315                 320
Glu Gly Thr Thr Tyr Gln Gln Ile Met Val Val Gly Ile Leu Cys Gly
                325                 330                 335
Ile Gly Phe Thr Met Ser Ile Phe Ile Ala Ser Leu Ala Phe Gly Ser
            340                 345                 350
Val Asp Pro Glu Leu Ile Asn Trp Ala Lys Leu Gly Ile Leu Val Gly
        355                 360                 365
Ser Ile Ser Ser Ala Val Ile Gly Tyr Ser Trp Leu Arg Val Arg Leu
    370                 375                 380
Arg Pro Ser Val
385

<210> SEQ ID NO 14
<211> LENGTH: 2958
<212> TYPE: DNA
<213> ORGANISM: Saccharomyces cerevisiae

<400> SEQUENCE: 14
atggctatct gggagcaact agaagtctca aaggcgcacg ttgcttatgc atgtgttggt     60
gtcttttcat ctatcttctc tttagtgtca ctttatgtca aggagaagct ttatattggt    120
gagtccaccg tagcaggtat atttgggcta attgtgggtc ctgtttgctt gaactggttt    180
aatcctctga atgggggaa ttcagacagt ataacattag agataacgag aatagtatta    240
tgtttgcaaa ttttttgccgt tgccgtggaa ctgccacgga aatatatgtt gaagcattgg    300
gtatctgtga cgatgctatt attgccagtg atgacagctg atggcttat tattggtctc    360 ttcgtttgga ttcttatacc tggcttgaat ttttctgcta gtttgttgat atctgcgtgc    420
attaccgcaa cagatcctat tctggcgcag tcggtcgtct ccggtaagtt tgcccaaaga    480
gtacctggtc acttaagaaa tctactgtct gcagagtcag gctgcaatga tggtatggcc    540 ttttcctttttt tatttctttc tatgaattta atcctacatc ccggtaatgg aagagaaatt    600
gtcaaagatt ggatttgcgt tactatcctg tatgagtgtt tgtttggatg cttgctaggt    660
tgcttcattg gttatgtagg cagaatcacc atcaggtttg ccgaaaagaa aacattatc    720 gatcgtgagt cgttcttagc attttacgtt gtcctggcgt tcatgtgtgc tgggttcggc    780
tccattttgg gtgtggatga cctattggta tcatttgcag ccggtgcgac tttcgcttgg    840
gatgggtggt tttctcaaaa gacacaagaa agtaatgttt ctaccgtgat tgatttgcta    900
ctaaactatg cgtattttat ctatttttggt gccattatac cttggagtca attcaacaac    960
```

```
ggtgaaattg gcacaaacgt ctggcgttta attatacttt cgatagtggt catcttttta    1020
cgtaggatcc ctgcagtcat gatattaaga cctcttatac ctgatataaa atcgtggcgt    1080
gaggcacttt ttgtgggcca ttttggtcct attggtgtag gtgcaatttt tgccgctata    1140
ctagctcgtg gagaattaga gtctacctt agtgacgaac ccactccttt aaatgttgta    1200
ccatcaaaag aggaaagtaa acattggcag ctgatagcct gtatatggcc ataacttgt    1260 tttttcattg ttacttctat catagttcat ggttcttcag ttgcaatcat aactctaggt    1320
cgtcatttga acacgataac gttaaccaaa acattcacta cacacaccac caatggtgat    1380
aatgggaaaa gttcatggat gcaaaggttg ccatcgttgg ataaagctgg acgatcattt    1440
tcattgcatc gtatggatac tcaaatgact ttatcagggg atgaaggtga agcagaagaa    1500
ggaggaggtc gtaagggact agcaggaggt gaagatgaag aaggattaaa caatgatcaa    1560
attggtagcg tcgcaacgag cggaattcct gcaagacccg ctggtggtat gccaaggagg    1620
aggaaattgt caagaaaaga gaaagattg aacagaagac agaaactgag aaacaaaggt    1680
agagaaatat tttcatcaag atctaaaaat gaaatgtatg atgacgatga gttgaatgat    1740
ctgggacgag aaaggttgca aaagaaaag gaagcacgcg ccgccacatt tgcattgagc    1800
acagccgtca atacacaacg taatgaggag attggaatgg gtggagatga agaagaagat    1860
gagtacacac cggaaaagga atatagcgat aattacaata acacaccaag ttttgagtcg    1920
tctgaaagat cttcatctct ccgaggaaga acttacgtac caagaaaccg ttacgatgga    1980
gaagagacag aaagcgagat tgaaagcgaa gacgagatgg aaaatgaaag tgaaagatca    2040
atggccagta gtgaagagag gagaattcga aaaatgaaag aggaagaaat gaaacctggt    2100
actgcttatt tagatggtaa tagaatgatt attgaaaata gcaaggtgaa aatcttgaat    2160
caagtagata tcgaggatcg caatgaggcg agagatgacg aagttagtgt tgatagtaca    2220
gcccattcaa gtttaactac cacaatgacc aatctatcca gtagtagtgg gggaaggtta    2280
aagagaattt taactcccac atcttttagga aagatacatt cattggttga taaaggaaag    2340
gataaaaata aaaacagcaa gtatcatgca tttaaaatag acaatctgtt aatcatcgag    2400
aatgaggacg gtgatgttat aaaaagatac aagataaatc ctcataaatc tgatgatgat    2460
aaaagtaaaa accgcccaag aaacgatagt gttgtatcaa gagctttaac agcagtagga    2520
ctaaagagca aagcgaacag cggcgtaccg cctccagtag atgaagaaaa agccatcgaa    2580
ggaccctcca ggaagggccc agggatgtta aagaaaagga cattaacacc tgcgccaccg    2640
agaggagttc aagattcctt agatctggaa gatgaacctt catctgagga ggatttaggt    2700
gatagttata acatggacga tagtgaagat tacgacgata atgcatatga atcagaaact    2760
gaattcgaaa gacaaagaag gttaaatgcg ttaggtgaga tgacggcacc agcggatcaa    2820
gatgacgaag agttgccgcc cttacctgtg gaggcacaaa caggaaacga tggtccaggt    2880
acagcggaag gaaaaaaaaa gcaaaagagt gctgctgtta agtcggcgct atcaaaaacg    2940
cttggtctca ataagtaa                                                 2958
```

<210> SEQ ID NO 15
<211> LENGTH: 985
<212> TYPE: PRT
<213> ORGANISM: Saccharomyces cerevisiae

<400> SEQUENCE: 15

```
Met Ala Ile Trp Glu Gln Leu Glu Val Ser Lys Ala His Val Ala Tyr
1               5                   10                  15
```

```
Ala Cys Val Gly Val Phe Ser Ser Ile Phe Ser Leu Val Ser Leu Tyr
             20                  25                  30

Val Lys Glu Lys Leu Tyr Ile Gly Glu Ser Thr Val Ala Gly Ile Phe
         35                  40                  45

Gly Leu Ile Val Gly Pro Val Cys Leu Asn Trp Phe Asn Pro Leu Lys
 50                  55                  60

Trp Gly Asn Ser Asp Ser Ile Thr Leu Glu Ile Thr Arg Ile Val Leu
 65                  70                  75                  80

Cys Leu Gln Ile Phe Ala Val Ala Val Glu Leu Pro Arg Lys Tyr Met
                 85                  90                  95

Leu Lys His Trp Val Ser Val Thr Met Leu Leu Leu Pro Val Met Thr
            100                 105                 110

Ala Gly Trp Leu Ile Ile Gly Leu Phe Val Trp Ile Leu Ile Pro Gly
        115                 120                 125

Leu Asn Phe Ser Ala Ser Leu Leu Ile Ser Ala Cys Ile Thr Ala Thr
130                 135                 140

Asp Pro Ile Leu Ala Gln Ser Val Val Ser Gly Lys Phe Ala Gln Arg
145                 150                 155                 160

Val Pro Gly His Leu Arg Asn Leu Leu Ser Ala Glu Ser Gly Cys Asn
                165                 170                 175

Asp Gly Met Ala Phe Pro Phe Leu Phe Leu Ser Met Asn Leu Ile Leu
            180                 185                 190

His Pro Gly Asn Gly Arg Glu Ile Val Lys Asp Trp Ile Cys Val Thr
        195                 200                 205

Ile Leu Tyr Glu Cys Leu Phe Gly Cys Leu Leu Gly Cys Phe Ile Gly
210                 215                 220

Tyr Val Gly Arg Ile Thr Ile Arg Phe Ala Glu Lys Lys Asn Ile Ile
225                 230                 235                 240

Asp Arg Glu Ser Phe Leu Ala Phe Tyr Val Val Leu Ala Phe Met Cys
                245                 250                 255

Ala Gly Phe Gly Ser Ile Leu Gly Val Asp Asp Leu Leu Val Ser Phe
            260                 265                 270

Ala Ala Gly Ala Thr Phe Ala Trp Asp Gly Trp Phe Ser Gln Lys Thr
        275                 280                 285

Gln Glu Ser Asn Val Ser Thr Val Ile Asp Leu Leu Leu Asn Tyr Ala
290                 295                 300

Tyr Phe Ile Tyr Phe Gly Ala Ile Ile Pro Trp Ser Gln Phe Asn Asn
305                 310                 315                 320

Gly Glu Ile Gly Thr Asn Val Trp Arg Leu Ile Ile Leu Ser Ile Val
                325                 330                 335

Val Ile Phe Leu Arg Arg Ile Pro Ala Val Met Ile Leu Arg Pro Leu
            340                 345                 350

Ile Pro Asp Ile Lys Ser Trp Arg Glu Ala Leu Phe Val Gly His Phe
        355                 360                 365

Gly Pro Ile Gly Val Gly Ala Ile Phe Ala Ala Ile Leu Ala Arg Gly
370                 375                 380

Glu Leu Glu Ser Thr Phe Ser Asp Glu Pro Thr Pro Leu Asn Val Val
385                 390                 395                 400

Pro Ser Lys Glu Glu Ser Lys His Trp Gln Leu Ile Ala Cys Ile Trp
                405                 410                 415

Pro Ile Thr Cys Phe Phe Ile Val Thr Ser Ile Val His Gly Ser
            420                 425                 430

Ser Val Ala Ile Ile Thr Leu Gly Arg His Leu Asn Thr Ile Thr Leu
```

-continued

```
            435                 440                 445
Thr Lys Thr Phe Thr Thr His Thr Thr Asn Gly Asp Asn Gly Lys Ser
450                 455                 460
Ser Trp Met Gln Arg Leu Pro Ser Leu Asp Lys Ala Gly Arg Ser Phe
465                 470                 475                 480
Ser Leu His Arg Met Asp Thr Gln Met Thr Leu Ser Gly Asp Glu Gly
                    485                 490                 495
Glu Ala Glu Glu Gly Gly Gly Arg Lys Gly Leu Ala Gly Gly Glu Asp
                500                 505                 510
Glu Glu Gly Leu Asn Asn Asp Gln Ile Gly Ser Val Ala Thr Ser Gly
            515                 520                 525
Ile Pro Ala Arg Pro Ala Gly Gly Met Pro Arg Arg Arg Lys Leu Ser
530                 535                 540
Arg Lys Glu Lys Arg Leu Asn Arg Arg Gln Lys Leu Arg Asn Lys Gly
545                 550                 555                 560
Arg Glu Ile Phe Ser Ser Arg Ser Lys Asn Glu Met Tyr Asp Asp Asp
                565                 570                 575
Glu Leu Asn Asp Leu Gly Arg Glu Arg Leu Gln Lys Glu Lys Glu Ala
                580                 585                 590
Arg Ala Ala Thr Phe Ala Leu Ser Thr Ala Val Asn Thr Gln Arg Asn
            595                 600                 605
Glu Glu Ile Gly Met Gly Gly Asp Glu Glu Asp Glu Tyr Thr Pro
610                 615                 620
Glu Lys Glu Tyr Ser Asp Asn Tyr Asn Asn Thr Pro Ser Phe Glu Ser
625                 630                 635                 640
Ser Glu Arg Ser Ser Ser Leu Arg Gly Arg Thr Tyr Val Pro Arg Asn
                645                 650                 655
Arg Tyr Asp Gly Glu Glu Thr Glu Ser Glu Ile Glu Ser Glu Asp Glu
            660                 665                 670
Met Glu Asn Glu Ser Glu Arg Ser Met Ala Ser Ser Glu Glu Arg Arg
            675                 680                 685
Ile Arg Lys Met Lys Glu Glu Glu Met Lys Pro Gly Thr Ala Tyr Leu
690                 695                 700
Asp Gly Asn Arg Met Ile Ile Glu Asn Lys Gln Gly Glu Ile Leu Asn
705                 710                 715                 720
Gln Val Asp Ile Glu Asp Arg Asn Glu Ala Arg Asp Asp Glu Val Ser
                725                 730                 735
Val Asp Ser Thr Ala His Ser Ser Leu Thr Thr Thr Met Thr Asn Leu
            740                 745                 750
Ser Ser Ser Ser Gly Gly Arg Leu Lys Arg Ile Leu Thr Pro Thr Ser
            755                 760                 765
Leu Gly Lys Ile His Ser Leu Val Asp Lys Gly Lys Asp Lys Asn Lys
            770                 775                 780
Asn Ser Lys Tyr His Ala Phe Lys Ile Asp Asn Leu Leu Ile Ile Glu
785                 790                 795                 800
Asn Glu Asp Gly Asp Val Ile Lys Arg Tyr Lys Ile Asn Pro His Lys
                805                 810                 815
Ser Asp Asp Asp Lys Ser Lys Asn Arg Pro Arg Asn Asp Ser Val Val
            820                 825                 830
Ser Arg Ala Leu Thr Ala Val Gly Leu Lys Ser Lys Ala Asn Ser Gly
            835                 840                 845
Val Pro Pro Pro Val Asp Glu Glu Lys Ala Ile Glu Gly Pro Ser Arg
850                 855                 860
```

```
Lys Gly Pro Gly Met Leu Lys Lys Arg Thr Leu Thr Pro Ala Pro Pro
865                 870                 875                 880

Arg Gly Val Gln Asp Ser Leu Asp Leu Glu Asp Glu Pro Ser Ser Glu
                885                 890                 895

Glu Asp Leu Gly Asp Ser Tyr Asn Met Asp Asp Ser Glu Asp Tyr Asp
            900                 905                 910

Asp Asn Ala Tyr Glu Ser Glu Thr Glu Phe Glu Arg Gln Arg Arg Leu
        915                 920                 925

Asn Ala Leu Gly Glu Met Thr Ala Pro Ala Asp Gln Asp Asp Glu Glu
    930                 935                 940

Leu Pro Pro Leu Pro Val Glu Ala Gln Thr Gly Asn Asp Gly Pro Gly
945                 950                 955                 960

Thr Ala Glu Gly Lys Lys Lys Gln Lys Ser Ala Ala Val Lys Ser Ala
            965                 970                 975

Leu Ser Lys Thr Leu Gly Leu Asn Lys
            980                 985
```